United States Patent [19]

Singer

[11] 4,248,620
[45] Feb. 3, 1981

[54] FUNGICIDAL AND HERBICIDAL 5-HALOAMINOALKYLIMINO-1,3-IMIDAZOLIDINE-2,4-DIONES

[75] Inventor: Malcolm S. Singer, Novato, Calif.

[73] Assignee: Chevron Research Company, San Francisco, Calif.

[21] Appl. No.: 81,709

[22] Filed: Oct. 4, 1979

[51] Int. Cl.³ .............. A01N 43/50; C07D 401/12; C07D 403/12; C07D 233/96
[52] U.S. Cl. .................. 71/92; 424/248.57; 424/267; 424/273 R; 544/139; 546/210; 548/307
[58] Field of Search .......... 546/210; 548/307; 71/92; 424/267, 273 R

[56] References Cited

U.S. PATENT DOCUMENTS

| | | | |
|---|---|---|---|
| 3,822,282 | 7/1974 | Singer | 548/307 |
| 3,992,402 | 11/1976 | Singer | 548/307 |

FOREIGN PATENT DOCUMENTS

| | | | |
|---|---|---|---|
| 815980 | 6/1974 | Belgium. | |
| 2107146 | 8/1972 | Fed. Rep. of Germany | 548/307 |
| 2013098 | 3/1970 | France | 548/307 |

*Primary Examiner*—Henry R. Jiles
*Assistant Examiner*—Richard A. Schwartz

*Attorney, Agent, or Firm*—D. A. Newell; T. G. DeJonghe; L. S. Squires

[57] ABSTRACT

A compound having the formula

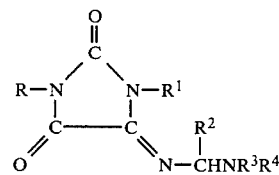

wherein R and $R^1$ is lower alkyl, lower alkenyl, lower alkynyl, lower alkoxyalkylene, cyclopentyl, or cyclohexyl, and the other is aryl or substituted aryl; $R^2$ is $C_1$–$C_2$ haloalkyl; $R^3$ and $R^4$ can, each independent of the other, be any of the substituents R and $R^1$ collectively can be and one of $R^3$ or $R^4$ can also be hydrogen or $R^3$ and $R^4$ together with the nitrogen atom to which they are joined can be piperidinyl, pyrrolidinyl or morpholinyl.

The compounds can be prepared by reaction of the corresponding 1'-chloroalkylimidazolidine with the appropriate primary or secondary amine.

The compounds are useful as fungicides and selective herbicides.

36 Claims, No Drawings

FUNGICIDAL AND HERBICIDAL 5-HALOAMINOALKYLIMINO-1,3-IMIDAZOLIDINE-2,4-DIONES

BACKGROUND OF THE INVENTION

1. Field of the Invention

This invention relates to 1-aryl-3-substituted-5-(1-amino or substituted amino-halo or polyhaloalkyl)imino-1,3-diazolidine-2,4-diones and salts thereof. In a further aspect the invention relates to herbicidal and/or fungicidal compositions containing such compounds. In a still further aspect the invention relates to the use of such compounds and compositions to prevent, reduce and/or control the growth of undesired vegetation and fungi.

2. The Prior Art

In my previous patent, U.S. Pat. No. 3,766,202, I disclose certain 1,3-disubstituted-5-(substituted-vinyl)imino-2,4-imidazolidine-1,3-diones which exhibited herbicidal activity and in my U.S. Pat. No. 3,992,402 I disclose certain 1,3-disubstituted-5-(1-hydroxy or halo-trihaloethyl)imino-1,3-imidazolidine-2,4-diones having herbicidal and fungicidal activity. In U.S. Pat. No. 3,925,553, I disclose certain 1,3-(disubstituted-5-trihaloethyl)imino-1,3-imidazolidine-2,4-diones also having herbicidal and fungicidal activities.

N-fluorophenylamino(trichloromethyl)methyleneaminde and derivatives thereof are discussed in Belgium Pat. No. 815,980. Chem Abstracts CA 72, 3053 s (1970) discloses that German Offenlengungsschriften No. 1,901,421 discloses certain substituted-N,N'bis(1-acylamino-2-trichloroethyl)-piperazines. Similarly, CA 90, 121657 u (1979) discloses that Czech Pat. No. 175,233 discloses certain N-(1-acylamino-2-trichloroethyl)-piperidines optionally containing a second hetero-ring atom.

SUMMARY OF THE INVENTION

The present invention provides certain 1-aryl-3-substituted-5-(1'-amino or substituted amino-trihaloalkyl)imino-1,3-diazolidine-2,4-diones having herbicidal activity and improved fungicidal activity, especially as regards Rhizoctonia as compared with the corresponding imino compounds of U.S. Pat. No. 3,925,553.

The compounds of the present invention can be represented by the following formula:

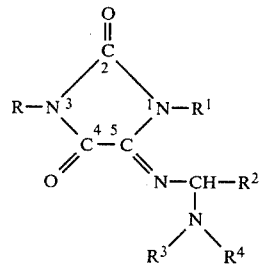

(I)

wherein one of R or $R^1$ is lower alkyl; lower alkenyl; lower alkynyl; lower alkoxyalkylene (e.g., methoxymethylene) cyclopentyl, cyclohexyl; and the other is aryl or substituted aryl having from 6 to 12 carbon atoms and optionally having 1 to 5 fluoro, chloro, or bromo atoms, 1 to 3 nitro groups, 1 to 3 alkyl groups having 1 to 4 carbon atoms, 1 or 2 trifluoromethyl groups, 1 or 2 cyano groups, 1 or 2 mono or di lower alkyl amino groups, 1 to 3 alkoxy groups having from 1 to 4 carbon atoms; 1 or 2 lower alkylsulfonyl, 1 or 2 lower alkylthio;

$R^2$ is halomethyl having from one through three substituents, each independently selected from the group of chloro and bromo or haloethyl having from 1 through 5 substituents independently selected from the group of chloro and bromo;

$R^3$ and $R^4$ are independently selected from the group of hydrogen and the same group of substituents as defined for R and $R^1$; provided, however, that only one of $R^3$ or $R^4$ can be hydrogen or $R^3$ and $R^4$ together with the nitrogen atom to which they are joined form a piperidinyl, pyrrolidinyl, or morpholinyl ring.

Compatible additional salts of the above compounds are also encompassed within the invention.

A further embodiment of the invention comprises herbicidal compositions and/or fungicidal compositions comprising the above compounds.

Another embodiment of the invention comprises the prevention, reduction or control of undesired vegetation and fungi.

The invention will be further described hereinbelow.

FURTHER DESCRIPTION OF THE INVENTION AND PREFERRED EMBODIMENTS

Considering now the invention in greater detail, typical illustrations of the compounds of the invention can be had by reference to Examples 1–7 set forth hereinbelow on pages 13–51. Also, as is apparent, the compounds have an asymmetric carbon atom and thus can exist as optical isomers. Accordingly, the respective optical isomers and geometric isomers as well as mixtures thereof are encompassed within the invention.

The preferred R substituents are methyl, ethyl, allyl and methoxymethylene. The preferred $R^1$ substituents are phenyl, 2-fluorophenyl, 3,5-dichlorophenyl, and trifluoromethylphenyl, the reverse R and $R^1$ position isomers are also preferred. The preferred $R^2$ substituents are trichloromethyl, bromodichloromethyl, 1,1-dichloroethyl, and chloromethyl. The preferred $R^3$ and $R^4$ substituents are those wherein one of $R^3$ or $R^4$ is hydrogen and the other is phenyl, 2-chlorophenyl, 3,4-dichlorophenyl, 2,4-dichlorophenyl, 2-fluorophenyl, and 4-fluorophenyl, or wherein each of $R^3$ and $R^4$ is methyl.

DEFINITIONS

As used herein the following terms have the following meanings, unless expressly stated to the contrary.

The term "alkyl" refers to both straight- and branched-chain alkyl groups. The term "lower alkyl" refers to both straight- and branched-chain alkyl groups having a total from 1 through 6 carbon atoms and includes primary, secondary and tertiary alkyl groups. Typical lower alkyls include, for example, methyl, ethyl, n-propyl, isopropyl, n-butyl, t-butyl, n-hexyl and the like.

The term "alkylene" refers to both straight- and branched-chained alkylene groups. The term lower alkylene refers to alkylene groups having from 1 through 6 carbon atoms. Typical alkylene groups include, for example, methylene, ethylene (i.e., —CH$_2$—CH$_2$—) 2-methylpropylene (i.e.,

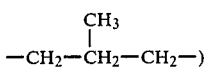

and the like.

The term "alkenyl" refers to unsaturated alkyl groups having a double bond (e.g., $CH_3CH=CH(CH_2)_2-$,) and includes both straight- and branched-chain alkenyl groups.

"Lower alkenyl" groups refer to alkenyl groups having from 2 through 6 carbon atoms. Typical lower alkenyl groups include, for example, ethylene; but-3-enyl; hex-4-enyl; 2-methylpent-4-enyl and the like.

The term "alkynyl" refers to unsaturated alkyl groups having a triple bond (e.g., $CH_3C\equiv C(CH_2)_2-$) and includes both straight- and branched-chain alkynyl groups.

The term "lower alkynyl" refers to alkynyl groups having from 2 through 6 carbon atoms and includes, for example, but-3-ynyl; hex-4-ynyl; 3-methylpent-4-ynyl and the like.

The term "halo or halogen atom" refers to the groups fluoro, chloro and bromo.

The term "alkoxy" refers to the group $R^1O-$ wherein $R^1$ is alkyl.

The term "lower alkoxy" refers to alkoxy groups having from 1 through 6 carbon atoms and includes, for example, methoxy, ethoxy, t-butoxy, hexoxy and the like.

The term "lower alkoxyalkylene" refers to groups wherein both the alkoxy group is a lower alkoxy group and the alkylene group is a lower alkylene group. Typical alkoxyalkylene groups include, for example, methoxymethylene, pentoxyhexylene and the like.

The term "aryl" refers to aryl groups having from 6 through 14 carbon atoms and includes, for example, phenyl, naphthyl, anthryl, phenanthryl and the like. The term "aryl(lower alkyl)" or "lower aralkyl" includes, for example, benzyl, phenethyl, naphthylethyl and the like.

The term "substituted aryl" refers to the radical having the general formula

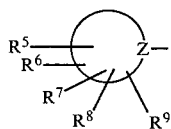

wherein

Z is aryl having 6-14 carbon atoms (e.g. phenyl, naphthyl, anthryl, phenanthryl, and preferably phenyl) and $R^5$ and $R^6$ are independently hydrogen, fluoro, chloro, bromo, nitro, $C_1-C_4$ alkyl, trifluoromethyl, cyano, lower alkyl amino, di(lower alkyl)amino, lower alkylsulfinyl, lower alkylsulfonyl, lower alkylthio or $C_1-C_4$ alkoxy;

$R^7$ is hydrogen, halo, nitro, $C_1-C_4$ alkyl or $C_1-C_4$ alkoxy;

$R^8$ and $R^9$ are independently selected from the group of hydrogen and halo, preferably hydrogen;

and wherein $R^5$, RHU 6, $R^7$, $R^8$ and $R^9$ can be at any available ring carbon atom and at least one of $R^5$, $R^6$, $R^7$, $R^8$, or $R^9$ is other than hydrogen.

Typical substituted aryl groups include, for example, 3,5-dichlorophenyl, 4-methoxyphenyl, 4-chloro-3-trifluoromethylphenyl, 3-methyl-4-nitrophenyl, and the like.

The term "di(lower alkyl)amino" refers to the group having the formula

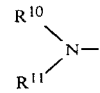

wherein $R^{10}$ and $R^{11}$ are independently selected from group of alkyl having 1 through 6 carbon atoms. Such groups include, for example, dimethylamino, diethylamino, N-methyl-N-hexylamino, and the like.

The compounds of the present invention can be prepared by the following process which can be conveniently represented by the following overall schematic reaction equation:

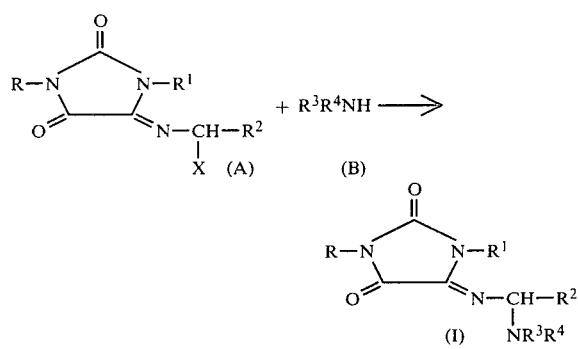

wherein X is chloro or bromo and R, $R^1$, $R^2$, $R^3$ and $R^4$ are as defined hereinabove.

This process can be conveniently effected by contacting the appropriate starting material of Formula A, having the desired R, $R^1$ and $R^2$ substituents, with the appropriate secondary or primary amine of Formula B having the appropriate $R^3$ and $R^4$ substituents, preferably in an inert organic solvent and in the presence of a scavenger base. This process is typically conducted at temperatures in the range of about from 0° to 80° C. and preferably about from 20° to 40° C., for about from 1 to 24 hours and preferably about from 1 to 4 hours. Typically a mol ratio of the compound of Formula A to the compound of Formula B in the range of about from 1 to 2 mols of compound of Formula B per mol of compound of Formula A and preferably about from 1 to 1.2 mols of compounds of Formula B per mol of compound of Formula A is used. Best results are typically obtained by conducting the process at temperatures in the range of about from 20° to 40° C. for about 1 to 2 hours using about a 1:1 mol ratio of compound of Formula B to compound of Formula A. Also, as is readily apparent, the reaction gives off hydrogen chloride or hydrogen bromide as a by-product. Accordingly, it is preferable to conduct the reaction in the presence of a suitable scavenger base, e.g., triethylamine, which reacts with the hydrogen chloride or hydrogen bromide byproduct. Other scavenger bases which could be used, include, for example, pyridine, 2,6-butadine, and the like. Typically, and preferably, the process is conducted in an inert organic solvent. Suitable inert organic solvents which can be used, include, for example, acetonitrile, 1,2-dimethoxyethane, methylene chloride, and the like and compatible mixtures thereof. Also, as can be expected optimum conditions will vary somewhat with the particular substrates used and can be determined by routine experimentation.

The compound of Formula 1 can be recovered by any suitable separation and purification procedure, such as, for example, recrystallization, and chromatography. Suitable separation and purification procedures, are, for example, illustrated in the Examples set forth herein below.

The starting materials of Formula A are generally known compounds and can be prepared according to known procedures, or by obvious modifications of such procedures; for example by the substitution of appropriate substrates and solvents, etc. The compounds of Formula A can, for example, be prepared by reacting the corresponding unsubstituted imino of Formula A with the corresponding acetylhalide or propenylhalide to yield the corresponding compound of Formula A having a 1-hydroxyalkylhalide substituent. This compound can in turn be reacted with the desired vinylchloride or vinylbromide to yield the corresponding compound of Formula A having a chloro or bromide substituent respectively at the 1- position of the alkylimino substituent. This procedure is, for example, described in U.S. Pat. No. 3,925,553.

Also, if desired, the acid addition salts of the compounds of Formula 1 can be prepared by carefully neutralizing the amino moiety of the compound with the appropriate acid. Other addition salts can then be made from this salt by ion exchange with a suitable ion exchange resin having the desired anionic form. Also, if desired, the respective optical isomers can be obtained by conventional resolution procedures, for example, by reacting the isomer mixture with an optically active acid which will yield a mixture of optical salts, of the desired compound, which can be resolved by conventional procedures (e.g., crystallization) into the respective plus and minus optical salts. The geometric isomers, for example, where $R^2$ is alkenyl, can be separated by conventional procedures.

It should also be appreciated that where typical preferred process conditions (e.g., reaction temperatures, times, mol ratios of reactants, solvents, etc.) have been given, that other process conditions could also be used, though typically with poor yields or economies.

UTILITY

The compounds of the invention exhibit substantial fungicidal activity against a variety of fungi, including rhizoctonia, moniliniа, helminthia, bean rust, celery late blight, and botrytis. Thus, the compounds can be applied to such fungi or to hosts which are subject to attack from such fungi, such as soil, and plants of the general grass family. The compounds can also be applied to combat fungus in domestic and industrial environments. The optimum dosage will, of course, vary with the particular fungi, host, and environment, but typically will be in the range of about from 100 to 1000 ppm by weight based on the weight of active ingredient to solvent.

The compounds could be applied directly to combat fungi but conveniently and typically are applied as fungicidal formulations comprising the compound(s) of the invention with a biologically inert solid or liquid. Generally the fungicide formulation contains the compounds of invention in amounts ranging from 0.005 to 95% by weight and preferably about from 1 to 50% by weight. These formulations are generally concentrates designed for further dilution prior to application.

Typical of the liquid carrier which can be admixed with the imidazolidinediones of this invention include liquids such as acetone, water, kerosene, xylene, alcohols, alkylated naphthylene and glycols. Typical solids which can be incorporated with the present compound include the natural clays such as kaolin clays and diatomaceous earth, synthetic fine silica, talc, pyrophyllite, etc.

The fungicidal formulations can also contain stabilizers, spreading agents, sticking agents, fillers, other compatible fungicides and pesticides, and the like.

At higher concentrations the compounds of the invention also exhibit both pre-emergent and post-emergent herbicidal activity against a variety of broad-leaved weeds, including mustard, pigweed, and lambsquarter. At relatively high concentrations the compounds also have pre-emergent herbicidal activity against a variety of grasses. Thus, the compounds can be applied as herbicides either directly or more pragmatically can be applied in a herbicidal composition comprising the active compound in an inert carrier or diluent.

Such herbicidal compositions comprise from about 0.01 to 95% by weight of the herbicidal compounds of the invention, intimately admixed with a biologically inert liquid or solid carrier, e.g., powders, dusts or granules. Suitable liquid diluents which can be used include, for example, water, organic solvents (e.g., hydrocarbons such as benzene, toluene, kerosene, diesel fuel, fuel oil, petroleum naphtha, etc.) and the like. Suitable solid carriers which can be used include, for example, natural clays (such as kaolin, attalpulgite, montmorillonite, etc.), talcs, pyrophyllite, diatomaceous silica, synthetic fine silica, calcium aluminosilicate, tricalcium phosphate, and the like. Also, organic materials, such as, for example, walnut shell flour, cottonseed hulls, wheat flour, wood flour, wood bark flour, and the like can also be used as carriers. The herbicidal composition typically also contains a small amount of one or more surface-active agents such as wetting agents, dispersing agents and can also contain compatible insecticides and additional compatible herbicides. The surface-active agent can either be anion, cationic or nonionic in character. The herbicidal composition can also contain compatible pesticides and adjuvants, stabilizers, conditioners, fillers, and if desired, other herbicidally active compounds, and the like.

The herbicidal compounds or the herbicidal compositions of the invention can be applied by conventional procedures which are well known by the art. For example, where the herbicide is applied in a pre-emergent application, it is applied directly to the area of soil desired to be protected. For post-emergent application, the herbicidal compositions will be applied directly to the foliage or other plant parts. The optimum amount of the herbicidal compound or composition will vary with the particular plant species, and the extent of part plant growth and the particular part of the plant which is contacted. The optimum dosage will also vary with the general location, or environment, of application (e.g., sheltered areas such as greenhouses compared to exposed areas such as fields), and type and degree of control desired. Generally, for both pre- and post-emergent control, the herbicidal compounds are applied at rates of about from 0.2 to 60 kg/ha, preferably about from 0.5 to 10 kg/ha.

A further understanding of the invention can be had in the following non-limiting Examples. Wherein, unless expressly stated to the contrary, all temperatures and temperature ranges refer to the Centigrade system and the term "ambient" or "room temperature" refers to about 20° C. The term "percent" or "%" refers to weight percent and the term "mol" or "mols" refers to gram mols. The term "equivalent" refers to a quantity of reagent equal in mols, to the mols of the preceding or succeeding reactant recited in that example in terms of finite mols or finite weight or volume. Also, unless expressly stated to the contrary, geometric isomer and racemic mixtures are used as starting materials and correspondingly isomer mixtures are obtained as products. Where given proton-magnetic resonance spectrum (p.m.r.) are determined at 60 mHz, and signals are assigned as singlets (s), broad singlets (bs), doublets (d), double doublets (dd), triplets (t), double triplets (dt), quartets (q) and multiplets (m).

PREPARATION A

This preparation illustrates the preparation of the starting materials of Formula A wherein R or $R^1$ is 2-fluorophenyl.

In this preparation 1-(2-fluorophenyl)-3-methyl-5-imino-1,3-imidazoladine-2,4-dione (10.0 g–0.045 mol) was slurried in 80 ml of 1,2-dimethoxyethane. Chloral (13.4 g–0.090 mol) was added, followed by the addition of 10.8 g (0.090 mol) of thionyl chloride. The reaction mixture became homogeneous as the temperature rose from the heat of reaction. The temperature was maintained at 35°–45° C. for one-half hour. The solvent was then removed from the mixture and the residue taken up in benzene. Filtration removed some high-melting white solids. Hexane was added to precipitate the product, which was then recovered by filtration and washed with ether affording 1-(2-fluorophenyl)-3-methyl-5-(1,2,2,2-tetrachloroethyl)imino-1,3-diazolidine-2,4-dione. The product melted at 175°–177° C. Elemental analysis showed: %C, calc. 37.2, found 37.5; %H, calc. 2.1, found 1.9; %N, calc. 10.9, found 10.9; %Cl, calc. 36.6, found 36.3.

Similarly, 1-(2-fluorophenyl)-3-methyl-5-(1,2,3,3,3-pentachloropropyl)imino-1,3-imidazolidine-2,4-dione is prepared by following the same procedure but replacing chloral with alpha,beta,beta,beta-tetrachloropropionic acid aldehyde (i.e., $Cl_3CCHClCHO$).

Similarly, 1-methyl-3-(2-fluorophenyl)-5-(1,2,2,2-tetrachloroethyl)imino-1,3-imidazolidine-2,4-dione and 1-methyl-3-(2-fluorophenyl)-5-(1,2,3,3,3-pentachloropropyl)imino-1,3-imidazolidine-2,4-dione are prepared by the above procedure by respectively replacing 1-(2-fluorophenyl)-3-methyl-5-imino-1,3-imidazolidine-2,4-dione with 1-methyl-3-(2-fluorophenyl)-3-methyl-5-imino-1,3-imidazolidine-2,4-dione.

PREPARATION B

This example illustrates the preparation of the starting materials of Formula A wherein $R^2$ is haloethyl.

In this preparation 1-methyl-3-phenyl-5-imino-1,3-diazolidine-2,4-dione (10.15 g; 0.05 mol) was dissolved in 80 ml 1,2-dimethoxyethane. Chloral (13.7 g, 1.0 mol) was added followed by the addition of thionyl chloride (11.9 g, 1.0 mol). The temperature of the reaction mixture rose to 45° C. due to the exothermicity of the reaction. One hour later the temperature was back to 23° C. and a solid had formed. The solid (1.1 g) had a melting point 140–150 with some not melting at all. The filtrate was stripped to give 9.6 g of a crude material which was recrystallized from benzene and washed with ether to give 8.2 g (0.02 mol) of 1-methyl-3-phenyl-5-(1,2,2,2-tetrachloroethyl)imino-1,3-diazolidine-2,4-dione melting at 158°–160° C.

Elemental analysis showed: %C calc. 39.06 found 39.2; %H calc. 2.46 found 2.3; %N, calc. 11.39 found 11.4; %Cl calc. 38.43 found 38.5.

Similarly, 1-methyl-3-phenyl-5-(1,2,2,trichloro-3,3,3-tribromopropyl)imino-1,3-diazolidine-2,4-dione is prepared by following the same procedure but replacing chloral with beta,beta,beta,tribromo-alpha,alpha-dichloropropionic and aldehyde.

Similarly, 1-phenyl-3-methyl-5-(1,2,2,2-tetrachloroethyl)imino-1,3-imidazolidine-2,4-dione and 1-phenyl-3-methyl-5-(1,2,2-trichloro-3,3,3-tribromopropyl)imino-1,3-imidazolidine-2,4-dione are prepared by the above procedure by respectively replacing 1-methyl-3-phenyl-5-imino-1,3-imidazolidine-2,4-dione with 1-phenyl-3-methyl-3-5-imino-1,3-imidazolidine-2,4-dione.

EXAMPLE 1

This example illustrates the preparation of the compounds of Formula 1 of the invention wherein $R^2$ is a halomethyl.

In this example 1-(2-fluorophenyl)-3-methyl-5-(1,2,2,2-tetrachloroethyl)imino-1,3-diazolidine-2,4-dione (7.75 g, 0.02 mol) was dissolved in 20 ml of acetonitrile, 2-fluoro aniline (2.2 g, 0.02 mol) was added. A mild exothermic reaction took place. After 10 minutes, triethylamine was added to the reaction mixture causing a very exothermic reaction to take place. Exothermicity subsided within the hour but stirring was continued for five hours. Ethyl ether (20 ml) was added to help precipitate the salts. The mixture was filtered and solvent was removed from the filtrate by high vacuum evaporation, thereby affording 1-(2-fluorophenyl)-3-methyl-5-(1-2'-fluorophenylamino-2,2,2-trichloroethyl)imino-1,3-diazolidine-2,4-dione identified its I.R. and p.m.r. spectera and the elemental analysis. (Anal. calcd. for $C_{18}H_{13}Cl_3F_2N_4O_2$; MW=461.69; C, 46.83; H, 2.84; N, 23.04 found; C, 45.6; H, 2.9; N, 22.7).

Similarly, by following the same procedure, but using the corresponding primary or secondary amines as starting materials in place of 2-fluorophenylamine, the following compounds are respectively prepared:

1-(2-fluorophenyl)-3-methyl-5-(1-phenylamino-2,2,2-trichloroethyl)imino-1,3-diazolidine-2,4-dione;

1-(2-fluorophenyl)-3-methyl-5-(1-3'-fluorophenylamino-2,2,2-trichloroethyl)imino-1,3-diazolidine-2,4-dione;

1-(2-fluorophenyl)-3-methyl-5-(1-4'-fluorophenylamino-2,2,2-trichloroethyl)imino-1,3-diazolidine-2,4-dione;

1-(2-fluorophenyl)-3-methyl-5-(1-2',4'-difluorophenylamino-2,2,2-trichloroethyl)imino-1,3-diazolidine-2,4-dione;

1-(2-fluorophenyl)-3-methyl-5-(1-3',4'-difluorophenylamino-2,2,2-trichloroethyl)imino-1,3-diazolidine-2,4-dione;

1-(2-fluorophenyl)-3-methyl-5-(1-2',3',4',5',6'-pentafluorophenylamino-2,2,2-trichloroethyl)imino-1,3-diazolidine-2,4-dione;

1-(2-fluorophenyl)-3-methyl-5-(1-2'-chlorophenylamino-2,2,2-trichloroethyl)imino-1,3-diazolidine-2,4-dione;

1-(2-fluorophenyl)-3-methyl-5-(1-4'-chloro-
phenylamino-2,2,2-trichloroethyl)imino-1,3-diazoli-
dine-2,4-dione;

1-(2-fluorophenyl)-3-methyl-5-(1-2'4'-dichloro-
phenylamino-2,2,2-trichloroethyl)imino-1,3-diazoli-
dine-2,4-dione-oil (Anal. calcd. for
$C_{18}H_{12}Cl_5FN_4O_2$—C42.18, H2.36, Cl34.55, N—10.93
found C43.2, H2.4, Cl33.35, N11.1);

1-(2-fluorophenyl)-3-methyl-5-(1-3'4'-dichloro-
phenylamino-2,2,2-trichloroethyl)imino-1,3-diazoli-
dine-2,4-dione oil (Anal. calcd. for
$C_8H_{12}Cl_5FN_4O_2$—C42.18, H2.26, Cl34.58, N10.93
found C44.4, H2.4, Cl32.6, N11.1);

1-(2-fluorophenyl)-3-methyl-5-(1-2'-bromo-
phenylamino-2,2,2-trichloroethyl)imino-1,3-diazoli-
dine-2,4-dione;

1-(2-fluorophenyl)-3-methyl-5-(1-3'4'-dibromo-
phenylamino-2,2,2-trichloroethyl)imino-1,3-diazoli-
dine-2,4-dione;

1-(2-fluorophenyl)-3-methyl-5-(1-3'-methylsulfinyl-
phenylamino-2,2,2-trichloroethyl)imino-1,3-diazoli-
dine-2,4-dione;

1-(2-fluorophenyl)-3-methyl-5-(1-4-ethylsulfonylamino-
2,2,2-trichloroethyl)imino-1,3-diazolidine-2,4-dione;

1-(2-fluorophenyl)-3-methyl-5-[1-(2-fluoro-3-bromo-4-
chlorophenylamino)-2,2,2-trichloroethyl]-imino-1,3-
diazolidine-2,4-dione;

1-(2-fluorophenyl)-3-methyl-5-(1-methylamino-2,2,2-
trichloroethyl)imino-1,3-diazolidine-2,4-dione;

1-(2-fluorophenyl)-3-methyl-5-(1-dimethylamino-2,2,2-
trichloroethyl)imino-1,3-diazolidine-2,4-dione-oil
(Anal. calcd. for $C_{14}H_{14}O_3FN_4O_2$—C42.50, H3.57,
Cl26.83, N14.16 found C47.6, H2.9, Cl 25.93, N12.2);

1-(2-fluorophenyl)-3-methyl-5-(1-t-butylamino-2,2,2-tri-
chloroethyl)imino-1,3-diazolidine-2,4-dione;

1-(2-fluorophenyl)-3-methyl-5-(1-prop-2'-enylamino-
2,2,2-trichloroethyl)imino-1,3-diazolidine-2,4-dione;

1-(2-fluorophenyl)-3-methyl-5-(1-but-3'-ynylamino-
2,2,2-trichloroethyl)imino-1,3-diazolidine-2,4-dione;

1-(2-fluorophenyl)-3-methyl-5-(1-cyclopentylamino-
2,2,2-trichloroethyl)imino-1,3-diazolidine-2,4-dione;

1-(2-fluorophenyl)-3-methyl-5-(1-2'-methyl-
phenylamino-2,2,2-trichloroethyl)imino-1,3-diazoli-
dine-2,4-dione;

1-(2-fluorophenyl)-3-methyl-5-(1-3'-propyl-
phenylamino-2,2,2-trichloroethyl)imino-1,3-diazoli-
dine-2,4-dione;

1-(2-fluorophenyl)-3-methyl-5-(1-4'-butylphenylamino-
2,2,2-trichloroethyl)imino-1,3-diazolidine-2,4-dione;

1-(2-fluorophenyl)-3-methyl-5-(1-4'-methoxy-
phenylamino-2,2,2-trichloroethyl)imino-1,3-diazoli-
dine-2,4-dione;

1-(2-fluorophenyl)-3-methyl-5-(1-3'-isopropoxy-
phenylamino-2,2,2-trichloroethyl)imino-1,3-diazoli-
dine-2,4-dione;

1-(2-fluorophenyl)-3-methyl-5-(1-2',4'-dimethoxyl-
phenylamino-2,2,2-trichloroethyl)imino-1,3-diazoli-
dine-2,4-dione;

1-(2-fluorophenyl)-3-methyl-5-(1-2'-nitrophenylamino-
2,2,2-trichloroethyl)imino-1,3-diazolidine-2,4-dione;

1-(2-fluorophenyl)-3-methyl-5-(1-2'-cyano-
phenylamino-2,2,2-trichloroethyl)imino-1,3-diazoli-
dine-2,4-dione;

1-(2-fluorophenyl)-3-methyl-5-(1-2'-trifluoromethyl-
phenylamino-2,2,2-trichloroethyl)imino-1,3-diazoli-
dine-2,4-dione;

1-(2-fluorophenyl)-3-methyl-5-(1-4'-trifluoromethyl-
phenylamino-2,2,2-trichloroethyl)imino-1,3-diazoli-
dine-2,4-dione;

1-(2-fluorophenyl)-3-methyl-5-[1-(2-methoxy-3-fluoro-
4-trifluoromethyl)phenylamino-2,2,2-trichloroethyl)-
]imino-1,3-dizolidine-2,4,dione;

1-(2-fluorophenyl)-3-methyl-5-(1-3'4'-ditrifluorome-
thylphenyl amino-2,2,2-trichloroethyl)imino-1,3-
diazolidine-2,4-dione;

1-(2-fluorophenyl)-3-methyl-5-[1-(2-methoxy-3-cyano-
4-trifluoromethyl)phenylamino-2,2,2-trichloroethyl-
]imino-1,3-diazolidine-2,4-dione;

1-(2-fluorophenyl)-3-methyl-5-[1-di(2,4-difluorophenyl-
)amino-2,2,2-trichloroethyl]imino-1,3-diazolidine-2,4-
dione;

1-(2-fluorophenyl)-3-methyl-5-[1-di(3,4-difluorophenyl-
)amino-2,2,2-trichloroethyl]imino-1,3-diazolidine-2,4-
dione;

1-(2-fluorophenyl)-3-methyl-5-[1-(N-methyl-N-
2',3',4',5',6'-pentafluorophenyl)amino-2,2,2-trichloro-
ethyl]imino-1,3-diazolidine-2,4-dione;

1-(2-fluorophenyl)-3-methyl-5-[1-(N-cyclohexyl-N-2'-
chlorophenyl)amino-2,2,2-trichloroethyl]imino-1,3-
diazolidine-2,4-dione;

1-(2-fluorophenyl)-3-methyl-5-[1-di(4'-chlorophenyl-
)amino-2,2,2-trichloroethyl]imino-1,3-diazolidine-2,4-
dione;

1-(2-fluorophenyl)-3-methyl-5-[1-(N-methyl-N-2',4'-
dichlorophenyl)amino-2,2,2-trichloroethyl]imino-
1,3-diazolidine-2,4-dione;

1-(2-fluorophenyl)-3-methyl-5-[1-di(3',4'-dichloro-
phenyl)amino-2,2,2-trichloroethyl]imino-1,3-diazoli-
dine-2,4-dione;

1-(2-fluorophenyl)-3-methyl-5-[1-di(2'-bromophenyl-
)amino-2,2,2-trichloroethyl]imino-1,3-diazolidine-2,4-
dione;

1-(2-fluorophenyl)-3-methyl-5-(1-(N-phenyl-N-3,4-
dibromophenyl)amino-2,2,2-trichloroethyl]imino-
1,3-diazolidine-2,4-dione;

1-(2-fluorophenyl)-3-methyl-5-[1-di(3'-methylsulfinyl-
phenyl)amino-2,2,2-trichloroethyl]imino-1,3-diazoli-
dine-2,4-dione;

1-(2-fluorophenyl)-3-methyl-5-[1-(N-methyl-N-4'-t-
butylsulfonylphenyl)amino-2,2,2-trichloroethyl-
]imino-1,3-diazolidine-2,4-dione;

1-(2-fluorophenyl)-3-methyl-5-[1-di(2-fluoro-3-bromo-
4-chlorophenyl)amino-2,2,2-trichloroethyl]-imino-
1,3-diazolidine-2,4-dione;

1-(2-fluorophenyl)-3-methyl-5-(1-methylthioamino-
2,2,2-trichloroethyl)imino-1,3-diazolidine-2,4-dione;

1-(2-fluorophenyl)-3-methyl-5-(1-N,N-dimethylthi-
oamino-2,2,2-trichloroethyl)imino-1,3-diazolidine-
2,4-dione;

1-(2-fluorophenyl)-3-methyl-5-(1-di-t-butylamino-2,2,2-
trichloroethyl)imino-1,3-diazolidine-2,4-dione;

1-(2-fluorophenyl)-3-methyl-5-(1-diphenylamino-2,2,2-
trichloroethyl)imino-1,3-diazolidine-2,4-dione;

1-(2-fluorophenyl)-3-methyl-5-[1-di(prop-2-enyl)amino-
2,2,2-trichloroethyl]imino-1,3-diazolidine-2,4-dione;

1-(2-fluorophenyl)-3-methyl-5-(1-dicyclopentylamino-
2,2,2-trichloroethyl)imino-1,3-diazolidine-2,4-dione;

1-(2-fluorophenyl)-3-methyl-5-[1-di(2-methylphenyl-
)amino-2,2,2-trichloroethyl]imino-1,3-diazolidine-2,4-
dione;

1-(2-fluorophenyl)-3-methyl-5-[1-(N-4-chlorophenyl-4-
methoxyphenyl)amino-2,2,2-trichloroethyl]imino-
1,3-diazolidine-2,4-dione;

1-(2-fluorophenyl)-3-methyl-5-(1-N-piperidinyl-2,2,2-trichloroethyl)imino-1,3-diazolidine-2,4-dione;

1-(2-fluorophenyl)-3-methyl-5-(1-N-pyrrolidinyl-2,2,2-trichloroethyl)imino-1,3-diazolidine-2,4-dione;

1-(2-fluorophenyl)-3-methyl-5-(1-N-morpholinyl-2,2,2-trichloroethyl)imino-1,3-diazolidine-2,4-dione;

1-(2-fluorophenyl)-3-methyl-5-[1-di(2-cyanophenyl)amino-2,2,2-trichloroethyl]imino-1,3-diazolidine-2,4-dione;

1-(2-fluorophenyl)-3-methyl-5-[1-(N-methyl-N-2'-trifluoromethylphenyl)amino-2,2,2-trichloroethyl]imino-1,3-diazolidine-2,4-dione; and 1-(2-fluorophenyl)-3-methyl-5-(1-2'-naphthylamino-2,2,2-trichloroethyl)imino-1,3-diazolidine-2,4-dione.

Similarly, by following the same procedure but replacing 1-2'-fluorophenyl-3-methyl-5-(1,2,2,2-tetrachloroethyl)imino-1,3-diazolidine-1,4-dione with 1-(2-fluorophenyl)-3-ethyl-5-(1,2,2,2-tetrachloroethyl)imino-1,3-diazolidine-2,4-dione;

1-(2-fluorophenyl)-3-prop-2'-enyl-5-(1,2,2,2-tetrachloroethyl)imino-1,3-diazolidine-2,4-dione;

1-(2-fluorophenyl)-3-but-3'-ynyl-5-(1,2,2,2-tetrachloroethyl)imino-1,3-diazolidine-2,4-dione;

1-(2-fluorophenyl)-3-cyclohexyl-5-(1,2,2,2-tetrachloroethyl)imino-1,3-diazolidine-2,4-dione; and 1-(2-fluorophenyl)-3-methoxymethylene-5-(1,2,2,2-tetrachloroethyl)imino-1,3-diazolidine-2,4-dione, the corresponding 3-ethyl; 3-prop-2-enyl; 3-but-3-ynyl; 3-cyclohexyl and 3-methoxymethylene analogs of each of the above preferred compounds are respectively prepared.

Similarly, the reverse 1-position-3-position isomers of each of the above prepared compounds are prepared by using the corresponding position isomers of formula A as the starting material. For example by using 1-methyl-3-(2-fluorophenyl)-5-(1,2,2,2-tetrachloroethyl)imino-1,3-diazolidine-2,4-dione in place of 1-(2-fluorophenyl)-3-methyl-5-(1,2,2,2-tetrachloroethyl)imino-1,3-diazolidine the following compounds (as well as the other position isomers of each of the above products) are prepared:

1-methyl-3-(2-fluorophenyl)-5-(1-2'-fluorophenylamino-2,2,2-trichloroethyl)imino-1,3-diazolidone-2,4-dione;

1-methyl-3-(2-fluorophenyl)-5-(1-phenylamino-2,2,2-trichloroethyl)imino-1,3-diazolidine-2,4-dione;

1-methyl-3-(2-fluorophenyl)-5-(1-2',4'-difluorophenylamino-2,2,2-trichloroethyl)imino-1,3-diazolidine-2,4-dione;

1-methyl-3-(2-fluorophenyl)-5-(1-4'-chlorophenylamino-2,2,2-trichloroethyl)imino-1,3-diazolidine-2,4-dione;

1-methyl-3-(2-fluorophenyl)-5-(1-2'-bromophenylamino-2,2,2-trichloroethyl)imino-1,3-diazolidine-2,4-dione;

1-methyl-3-(2-fluorophenyl)-5-[1-(2-fluoro-3-bromo-4-chlorophenylamino)-2,2,2-trichloroethyl]-imino-1,3-diazolidine-2,4-dione;

1-methyl-3-(2-fluorophenyl)-5-(1-prop-2'-enylamino-2,2,2-trichloroethyl)imino-1,3-diazolidine-2,4-dione;

1-methyl-3-(2-fluorophenyl)-5-(1-3'-propylphenylamino-2,2,2-trichloroethyl)imino-1,3-diazolidine-2,4-dione;

1-methyl-3-(2-fluorophenyl)-5-(1-2',4'-dimethoxyphenylamino-2,2,2-trichloroethyl)imino-1,3-diazolidine-2,4-dione;

1-methyl-3-(2-fluorophenyl)-5-(1-4'-trifluoromethylphenylamino-2,2,2-trichloroethyl)imino-1,3-diazolidine-2,4-dione;

EXAMPLE 2

This example illustrates further the preparation of the compounds of Formula 1.

In this Example 1-phenyl-3-methyl-5-(1,2,2,2-tetrachloroethyl)imino-1,3-diazolidine-2,4-dione (0.02 mol) was dissolved in 20 ml of acetonitrile and 0.02 mol of aniline then added. A mild exothermic reaction was observed. After ten minutes, triethylamine was added causing a very exothetmic reaction, which subsided within an hour to occur. The mixture was stirred for five hours and then 20 ml of ethyl ether added to assist precipitation of salts. The mixture was filtered and the filtrate evaporated off under high vacuum affording 1-phenyl-3-methyl-5-(1-phenylamino-2,2,2-trichloroethyl)imino-1,3-diazolidine-2,4-dione oil (Anal. calcd. for $C_{18}H_{15}Cl_3N_4O_2$—C50.79, H3.55, Cl24.98, N13.16 found C51.6, H3.8, Cl26.54, N12.2.

Similarly by following the same procedure but using the corresponding primary or secondary amine starting materials in place of 2-fluorophenylamine, the following compounds are respectively prepared:

1-phenyl-3-methyl-5-(1-2'-fluorophenylamino-2,2,2-trichloroethyl)-imino-1,3-diazolidine-2,4-dione;

1-phenyl-3-methyl-5-(1-3'-fluorophenylamino-2,2,2-trichloroethyl)imino-1,3-diazolidine-2,4-dione;

1-phenyl-3-methyl-5-(1-4'-fluorophenylamino-2,2,2-trichloroethyl)imino-1,3-diazolidine-2,4-dione;

1-phenyl-3-methyl-5-(1-2',4'-dichlorophenylamino-2,2,2-trichloroethyl)imino-1,3-diazolidine-2,4-dione-oil (and called for $C_{18}H_{13}Cl_5H_4O_2$, C43.71, H2.65, Cl35.84, N11.33 found C44.7, H2.3, Cl34.3, N11.8);

1-phenyl-3-methyl-5-(1-3',4'-dichlorophenylamino-2,2,2-trichloroethyl)imino-1,3-diazolidine-2,4-dione-oil (Anal. calcd. for $C_{18}H_{13}Cl_5N_4O_2$—C43.71, H2.65, Cl35.84, N11.33 found C40.0, H2.2, Cl35.5, N10.4);

1-phenyl-3-methyl-5-(1-2',3',4',5',6'-pentafluorophenylamino-2,2,2-trichloroethyl)imino-1,3-diazolidine-2,4-dione;

1-phenyl-3-methyl-5-(1-2'-chlorophenylamino-2,2,2-trichloroethyl)imino-1,3-diazolidine-2,4-dione;

1-phenyl-3-methyl-5-(1-4'-chlorophenylamino-2,2,2-trichloroethyl)imino-1,3-diazolidine-2,4-dione;

1-phenyl-3-methyl-5-(1-2',4'-difluorophenylamino-2,2,2-trichloroethyl)imino-1,3-diazolidine-2,4-dione;

1-phenyl-3-methyl-5-(1-3',4'-difluorophenylamino-2,2,2-trichloroethyl)imino-1,3-diazolidine-2,4-dione;

1-phenyl-3-methyl-5-(1-2'-bromophenylamino-2,2,2-trichloroethyl)imino-1,3-diazolidine-2,4-dione;

1-phenyl-3-methyl-5-(1-3',4'-dibromophenylamino-2,2,2-trichloroethyl)imino-1,3-diazolidine-2,4-dione;

1-phenyl-3-methyl-5-(1-2'-methythiophenylamino-2,2,2-trichloro-ethyl)imino-1,3-diazolidine-2,4-dione;

1-phenyl-3-methyl-5-(1-2',4'-dimethylsulfonylphenylamino-2,2,2-trichloroethyl)imino-1,3-diazolidine-2,4-dione;

1-phenyl-3-methyl-5-[1-(2-fluoro-3-bromo-4-chlorophenylamino)-2,2,2-trichloroethyl]imino-1,3-diazolidine-2,4-dione;

1-phenyl-3-methyl-5-(1-methylamino-2,2,2-trichloroethyl)imino-1,3-diazolidine-2,4-dione;

1-phenyl-3-methyl-5-(1-dimethylamino-2,2,2-trichloroethyl)imino-1,3-diazolidine-2,4-dione;

1-phenyl-3-methyl-5-(1-t-butylamino-2,2,2-trichloroethyl)imino-1,3-diazolidine-2,4-dione;

1-phenyl-3-methyl-5-(1-prop-2'-enylamino-2,2,2-trichloroethyl)imino-1,3-diazolidine-2,4-dione;
1-phenyl-3-methyl-5-(1-but-3'-ynylamino-2,2,2-trichloroethyl)imino-1,3-diazolidine-2,4-dione;
1-phenyl-3-methyl-5-(1-cyclopentylamino-2,2,2-trichloroethyl)imino-1,3-diazolidine-2,4-dione;
1-phenyl-3-methyl-5-(1-2'-methylphenylamino-2,2,2-trichloroethyl)imino-1,3-diazolidine-2,4-dione;
1-phenyl-3-methyl-5-(1-3'-propylphenylamino-2,2,2-trichloroethyl)imino-1,3-diazolidine-2,4-dione;
1-phenyl-3-methyl-5-(1-4'-t-butylphenylamino-2,2,2-trichloroethyl)imino-1,3-diazolidine-2,4-dione;
1-phenyl-3-methyl-5-(1-4'-methoxyphenylamino-2,2,2-trichloroethyl)imino-1,3-diazolidine-2,4-dione;
1-phenyl-3-methyl-5-(1-3'-isopropoxyphenylamino-2,2,2-trichloroethyl)imino-1,3-diazolidine-2,4-dione;
1-phenyl-3-methyl-5-(1-2',4'-dimethoxylphenylamino-2,2,2-trichloroethyl)imino-1,3-diazolidine-2,4-dione;
1-phenyl-3-methyl-5-(1-2'-nitrophenylamino-2,2,2-trichloroethyl)imino-1,3-diazolidine-2,4-dione;
1-phenyl-3-methyl-5-(1-2'-cyanophenylamino-2,2,2-trichloroethyl)imino-1,3-diazolidine-2,4-dione;
1-phenyl-3-methyl-5-(1-2'-trifluoromethylphenylamino-2,2,2-trichloroethyl)imino-1,3-diazolidine-2,4-dione;
1-phenyl-3-methyl-5-(1-4'-trifluoromethylphenylamino-2,2,2-trichloroethyl(imino-1,3-diazolidine-2,4-dione;
1-phenyl-3-methyl-5-[1-(2'-methoxy-3'-fluoro-4'-trifluoromethyl)phenylamino-2,2,2-trichloroethyl)]-imino-1,3-diazolidine-2,4-dione;
1-phenyl-3-methyl-5-(1-3',4'-ditrifluoromethylphenylamino-2,2,2-trichloroethyl)-imino-1,3-diazolidine;
1-phenyl-3-methyl-5-(1-diphenylamino-2,2,2-trichloroethyl)imino-1,3-diazolidine-2,4-dione;
1-phenyl-3-methyl-5-[1-di(2'-fluorophenyl)amino-2,2,2-trichloroethyl]imino-1,3-diazolidine-2,4-dione;
1-phenyl-3-methyl-5-[1-(N-methyl-N-4-fluorophenyl)amino-2,2,2-trichloroethyl]imino-1,3-diazolidine-2,4-dione;
1-phenyl-3-methyl-5-[1-(N-methyl-N-2',4'-difluorophenylamino-2,2,2-trichloroethyl]imino-1,3-diazolidine-2,4-dione;
1-phenyl-3-methyl-5-[1-di(3',4'-difluorophenyl)amino-2,2,2-trichloroethyl]imino-1,3-diazolidine-2,4-dione;
1-phenyl-3-methyl-5-[1-di(4-chlorophenyl)amino-2,2,2-trichloroethyl]imino-1,3-diazolidine-2,4-dione;
1-phenyl-3-methyl-5-[1-(N-methyl-N-2,4-dichlorophenyl)amino-2,2,2-trichloroethyl]imino-1,3-diazolidine-2,4-dione;
1-phenyl-3-methyl-5-[1-(N-methyl-N-3,4-dichlorophenyl)amino-2,2,2-trichloroethyl]imino-1,3-diazolidine-2,4-dione;
1-phenyl-3-methyl-5-[1-di(2-bromophenyl)amino-2,2,2-trichloroethyl]imino-1,3-diazolidine-2,4-dione;
1-phenyl-3-methyl-5-[1-di(2-methylsulfonylphenyl)amino-2,2,2-trichloro-ethyl]imino-1,3-diazolidine-2,4-dione;
1-phenyl-3-methyl-5-[1-di(prop-2'-enyl)amino-2,2,2-trichloroethyl]imino-1,3-diazolidine-2,4-dione;
1-phenyl-3-methyl-5-[1-di(but-3'-ynyl)amino-2,2,2-trichloroethyl]imino-1,3-diazolidine-2,4-dione;
1-phenyl-3-methyl-5-[1-di(cyclohexylamino)-2,2,2-trichloroethyl]imino-1,3-diazolidine-2,4-dione;
1-phenyl-3-methyl-5-[1-di(2-methylphenyl)amino-2,2,2-trichloroethyl]imino-1,3-diazolidine-2,4-dione;
1-phenyl-3-methyl-5-(1-N-piperidinyl-2,2,2-trichloroethyl)imino-1,3-diazolidine-2,4-dione;
1-phenyl-3-methyl-5-(1-N-pyrrolidinyl-2,2,2-trichloroethyl)imino-1,3-diazolidine-2,4-dione;
1-phenyl-3-methyl-5-(1-N-morpholinyl-2,2,2-trichloroethyl)imino-1,3-diazolidine-2,4-dione;
1-phenyl-3-methyl-5-(1-3'-isopropoxyphenylamino-2,2,2-trichloroethyl)imino-1,3-diazolidine-2,4-dione;
1-phenyl-3-methyl-5-[1-di(2,4-diethoxylphenyl)amino-2,2,2-trichloroethyl]imino-1,3-diazolidine-2,4-dione;
1-phenyl-3-methyl-5-[1-di(2'-nitrophenyl)amino-2,2,2-trichloro-ethyl]imino-1,3-diazolidine-2,4-dione;
1-phenyl-3-methyl-5-(1-2'-cyanophenylamino-2,2,2-trichloroethyl)imino-1,3-diazolidine-2,4-dione;
1-phenyl-3-methyl-5-(1-2'-trifluoromethylphenylamino-2,2,2-trichloroethyl)imino-1,3-diazolidine-2,4-dione;
1-phenyl-3-methyl-5-[1-(N-methyl-2,4-trifluoromethylphenyl)amino-2,2,2-trichloroethyl]imino-1,3-diazolidine-2,4-dione.

Similarly, by following the same procedure but replacing 1-phenyl-3-methyl-5-(1,2,2,2-tetrachloroethyl)imino-1,3-diazolidine-1,4-dione with
1-phenyl-3-ethyl-5-(1,2,2,2-tetrachloroethyl)imino-1,3-diazolidine-2,4-dione;
1-phenyl-3-prop-2'-enyl-5-(1,2,2,2-tetrachloroethyl)imino-1,3-diazolidine-2,4-dione;
1-phenyl-3-but-3'-ynyl-5-(1,2,2,2-tetrachloroethyl)imino-1,3-diazolidine-2,4-dione;
1-phenyl-3-cyclohexyl-5-(1,2,2,2-tetrachloroethyl)imino-1,3-diazolidine-2,4-dione, and
1-phenyl-3-methoxymethylene-5-(1,2,2,2-tetrachloroethyl)imino-1,3-diazolidine-2,4-dione, the corresponding 3-ethyl; 3-prop-2-enyl; 3-but-3-ynyl; 3-cyclohexyl and 3-methoxymethylene analogs of each of the above-named compounds are respectively prepared.

Similarly the reverse 1-position-3-position isomers of each of the above prepared compounds are prepared by using the corresponding position isomer of formula A as the starting material. For example by using 1-methyl-3-phenyl-5-(1,2,2,2-tetrachloroethyl)imino-1,3-diazolidine-2,4-dione in place of 1-phenyl-3-methyl-5-(1,2,2,2-tetrachloroethyl)imino-1,3-diazolidine the following compounds (as well as the other 1-3 position isomers of each of the above products) are prepared:
1-methyl-3-phenyl-5-(1-2'fluorophenylamino-2,2,2 trichloroethyl)imino-1,3-diazolidine-2,4-dione;
1-methyl-3-phenyl-5-(1-diphenylamino-2,2,2-trichloroethyl)imino-1,3-diazolidine-2,4-dione;
1-methyl-3-phenyl-5-[1-(N-methyl-N-2',4'difluorophenyl)amino-2,2,2-trichloroethyl]imino-1,3-diazolidine-2,4-dione;
1-methyl-3-phenyl-5-[1-di(4-chlorophenyl)amino-2,2,2-trichloroethyl]imino-1,3-diazolidine-2,4-dione;
1-methyl-3-phenyl-5-[1-di(2-methylsulfonyl)amino-2,2,2-trichloroethyl]imino-1,3-diazolidine-2,4-dione;
1-methyl-3-phenyl-5-[1-di(2-methylphenyl)amino-2,2,2-trichloroethyl]imino-1,3-diazolidine-2,4-dione;
1-methyl-3-phenyl-5-(1-3'isopropoxyphenylamino-2,2,2-trichloroethyl)imino-1,3-diazolidine-2,4-dione;
1-methyl-3-phenyl-5-(1-2'-trifluoromethylphenylamino-2,2,2-trichloroethyl)imino-1,3-diazolidine-2,4-dione.

EXAMPLE 3

This example illustrates further the preparation of the compounds of Formula 1.

In this Example 1-(3-trifluoromethylphenyl)-3-methyl-5-(1,2,2,2-tetrachloroethyl)imino-1,3-diazolidine-2,4-dione; (0.05 mol) is dissolved in 20 ml of acetonitrile. One equivalent of 2-fluoroaniline (0.05 mol) is added with stirring over a five minute period. Temperature is maintained at 25°–35° C. Triethylamine (0.05 mol) is then added with stirring over a 10-minute period. The temperature is maintained at 25°–35° C. for one hour. Methylene chloride (50 ml) is added and the solution is washed 3 times with 50 ml of water, dried over magnesium sulfate and filtered. The solvent is removed under high vacuum affording 1-(3-trifluoromethylphenyl)-3-methyl-5-(1-2'-fluorophenylamino-2,2,2-trichloroethyl)imino-1,3-diazolidine-2,4-dione.

Following the same procedure but using the corresponding primary or secondary amine starting materials in place of 2-fluorophenylamine (i.e., 2-fluoroaniline), the following compounds are respectively prepared:

1-(3-trifluoromethylphenyl)-3-methyl-5-(1-phenylamino-2,2,2-trichloroethyl)imino-1,3-diazolidine-2,4-dione;

1-(3-trifluoromethylphenyl)-3-methyl-5-(1-3'-fluorophenylamino-2,2,2-trichloroethyl)imino-1,3-diazolidine-2,4-dione;

1-(3-trifluoromethylphenyl)-3-methyl-5-(1-4'-fluorophenylamino-2,2,2-trichloroethyl)imino-1,3-diazolidine-2,4-dione;

1-(3-trifluoromethylphenyl)-3-methyl-5-(1-2',4'-difluorophenylamino-2,2,2-trichloroethyl)imino-1,3-diazolidine-2,4-dione;

1-(3-trifluoromethylphenyl)-3-methyl-5-(1-3',4'-difluorophenylamino-2,2,2-trichloroethyl)imino-1,3-diazolidine-2,4-dione;

1-(3-trifluoromethylphenyl)-3-methyl-5-(1-2',3',4',5',6'-pentafluorophenylamino2,2,2-trichloroethyl)imino-1,3-diazolidine-2,4-dione;

1-(3-trifluoromethylphenyl)-3-methyl-5-(1-2'-chlorophenylamino-2,2,2-trichloroethyl)imino-1,3-diazolidine-2,4-dione;

1-(3-trifluoromethylphenyl)-3-methyl-5-(1-4'-chlorophenylamino-2,2,2-trichloroethyl)imino-1,3-diazolidine-2,4-dione;

1-(3-trifluoromethylphenyl)-3-methyl-5-(1-2',4'-dichlorophenylamino-2,2,2-trichloroethyl)imino-1,3-diazolidine-2,4-dione;

1-(3-trifluoromethylphenyl)-3-methyl-5-(1-3',4'-dichlorophenylamino-2,2,2-trichloroethyl)imino-1,3-diazolidine-2,4-dione;

1-(3-trifluoromethylphenyl)-3-methyl-5-(1-2'-bromophenylamino-2,2,2-trichloroethyl)imino-1,3-diazolidine-2,4-dione;

1-(3-trifluoromethylphenyl)-3-methyl-5-(1-3',4'-dibromophenylamino-2,2,2-trichloroethyl)imino-1,3-diazolidine-2,4-dione;

1-(3-trifluoromethylphenyl)-3-methyl-5-(1-2'-ethylthiophenylamino-2,2,2-trichloroethyl)imino-1,3-diazolidine-2,4-dione;

1-(3-trifluoromethylphenyl)-3-methyl-5-(1-2',4'-dimethylsulfinylphenylamino-2,2,2-trichloroethyl)imino-1,3-diazolidine-2,4-dione;

1-(3-trifluoromethylphenyl)-3-methyl-5-[1-(2-fluoro-3-bromo-4-chloro)phenylamino-2,2,2-trichloroethyl)]-2,2,2-trichloroethyl)imino-1,3-diazolidine-2,4-dione;

1-(3-trifluoromethylphenyl)-3-methyl-5-(1-methylamino-2,2,2-trichloroethyl)imino-1,3-diazolidine-2,4-dione;

1-(3-trifluoromethylphenyl)-3-methyl-5-(1-dimethylamino-2,2,2-trichloroethyl)imino-1,3-diazolidine-2,4-dione;

1-(3-trifluoromethylphenyl)-3-methyl-5-(1-t-butylamino-2,2,2-trichloroethyl)imino-1,3-diazolidine-2,4-dione;

1-(3-trifluoromethylphenyl)-3-methyl-5-(1-prop-2'-enylamino-2,2,2-trichloroethyl)imino-1,3-diazolidine-2,4-dione;

1-(3-trifluoromethylphenyl)-3-methyl-5-(1-but-3'-ynylamino-2,2,2-trichloroethyl)imino-1,3-diazolidine-2,4-dione;

1-(3-trifluoromethylphenyl)-3-methyl-5-(1-cyclopentylamino-2,2,2-trichloroethyl)imino-1,3-diazolidine-2,4-dione;

1-(3-trifluoromethylphenyl)-3-methyl-5-(1-2'-methylphenylamino-2,2,2-trichloroethyl)imino-1,3-diazolidine-2,4-dione;

1-(3-trifluoromethylphenyl)-3-methyl-5-(1-3'-propylphenylamino-2,2,2-trichloroethyl)imino-1,3-diazolidine-2,4-dione;

1-(3-trifluoromethylphenyl)-3-methyl-5-(1-4'-t-butylphenylamino-2,2,2-trichloroethyl)imino-1,3-diazolidine-2,4-dione;

1-(3-trifluoromethylphenyl)-3-methyl-5-(1-4'-methoxyphenylamino-2,2,2-trichloroethyl)imino-1,3-diazolidine-2,4-dione;

1-(3-trifluoromethylphenyl)-3-methyl-5-(1-3'-isopropoxyphenylamino-2,2,2-trichloroethyl)imino-1,3-diazolidine-2,4-dione;

1-(3-trifluoromethylphenyl)-3-methyl-5-(1-2',4'-dimethoxyphenylamino-2,2,2-trichloroethyl)imino-1,3-diazolidine-2,4-dione;

1-(3-trifluoromethylphenyl)-3-methyl-5-(1-2'-nitrophenylamino-2,2,2-trichloroethyl)imino-1,3-diazolidine-2,4-dione;

1-(3-trifluoromethylphenyl)-3-methyl-5-(1-2'-cyanophenylamino-2,2,2-trichloroethyl)imino-1,3-diazolidine-2,4-dione;

1-(3-trifluoromethylphenyl)-3-methyl-5-(1-2'-trifluoromethylphenylamino-2,2,2-trichloroethyl)imino-1,3-diazolidine-2,4-dione;

1-(3-trifluoromethylphenyl)-3-methyl-5-(1-4'-trifluoromethylphenylamino-2,2,2-trichloroethyl)imino-1,3-diazolidine-2,4-dione;

1-(3-trifluoromethylphenyl)-3-methyl-5-[1-(2'-methoxy-3'-fluoro-4'-trifluoromethyl)phenylamino-2,2,2-trichloroethyl)]imino-1,3-diazolidine-2,4-dione;

1-(3-trifluoromethylphenyl)-3-methyl-5-(1,3',4-ditrifluorophenylamino-2,2,2-trichloroethyl)imino-1,3-diazolidine-2,4-dione;

1-(3-trifluoromethylphenyl)-3-methyl-5-[1-(N-methyl-N-phenyl)amino-2,2,2-trichloroethyl]imino-1,3-diazolidine-2,4-dione;

1-(3-trifluoromethylphenyl)-3-methyl-5-[1-(N-methyl-N-2-fluorophenyl)amino-2,2,2-trichloroethyl]imino-1,3-diazolidine-2,4-dione;

1-(3-trifluoromethylphenyl)-3-methyl-5-[1-di(3'-fluorophenyl)amino-2,2,2-trichloroethyl]imino-1,3-diazolidine-2,4-dione;

1-(3-trifluoromethylphenyl)-3-methyl-5-[1-(N-methyl-N-2,4-difluorophenyl)amino-2,2,2-trichloroethyl]imino-1,3-diazolidine-2,4-dione;

1-(3-trifluoromethylphenyl)-3-methyl-5-[1-(N-methyl-N-2'-chlorophenyl)amino-2,2,2-trichloroethyl]imino-1,3-diazolidine-2,4-dione;

1-(3-trifluoromethylphenyl)-3-methyl-5-[1-di(2-chlorophenyl)amino-2,2,2-trichloroethyl]imino-1,3-diazolidine-2,4-dione;

1-(3-trifluoromethylphenyl)-3-methyl-5-[1-(N-methyl-N-2,4-dichlorophenyl)amino-2,2,2-trichloroethyl]imino-1,3-diazolidine-2,4-dione;

1-(3-trifluoromethylphenyl)-3-methyl-5-[1-di(2,4-dichlorophenyl)amino-2,2,2-trichloroethyl]imino-1,3-diazolidine-2,4-dione;

1-(3-trifluoromethylphenyl)-3-methyl-5-[1-di(2-bromophenyl)amino-2,2,2-trichloroethyl]imino-1,3-diazolidine-2,4-dione;

1-(3-trifluoromethylphenyl)-3-methyl-5-[1-di(2-methylsulfonylphenyl)amino-2,2,2-trichloroethyl]imino-1,3-diazolidine-2,4-dione;

1-(3-trifluoromethylphenyl)-3-methyl-5-(1-N-piperidinylphenylamino-2,2,2-trichloroethyl)imino-1,3-diazolidine-2,4-dione;

1-(3-trifluoromethylphenyl)-3-methyl-5-[1-N-pyrrolidinyl-4-chloro)phenylamino-2,2,2-trichloroethyl)]-2,2,2-trichloroethyl)imino-1,3-diazolidine-2,4-dione;

1-(3-trifluoromethylphenyl)-3-methyl-5-(1-N-morpholinyl-2,2,2-trichloroethyl)imino-1,3-diazolidine-2,4-dione;

1-(3-trifluoromethylphenyl)-3-methyl-5-[1-(N-methyl-N-prop-2'-enyl)amino-2,2,2-trichloroethyl]imino-1,3-diazolidine-2,4-dione;

1-(3-trifluoromethylphenyl)-3-methyl-5-[1-(N-methyl-N-but-3'-ynyl)amino-2,2,2-trichloroethyl]imino-1,3-diazolidine-2,4-dione;

1-(3-trifluoromethylphenyl)-3-methyl-5-[1-(N-methyl-N-cyclopentyl)amino-2,2,2-trichloroethyl]imino-1,3-diazolidine-2,4-dione;

1-(3-trifluoromethylphenyl)-3-methyl-5-[1-di(2-methylphenyl)amino-2,2,2-trichloroethyl]imino-1,3-diazolidine-2,4-dione;

1-(3-trifluoromethylphenyl)-3-methyl-5-[1-di(2'-methoxyphenyl)amino-2,2,2-trichloroethyl]imino-1,3-diazolidine-2,4-dione;

1-(3-trifluoromethylphenyl)-3-methyl-5-[1-(N-methyl-N-2',4'-dimethoxylphenyl)amino-2,2,2-trichloroethyl]imino-1,3-diazolidine-2,4-dione;

1-(3-trifluoromethylphenyl)-3-methyl-5-[1-di(2-nitrophenyl)amino-2,2,2-trichloroethyl]imino-1,3-diazolidine-2,4-dione;

1-(3-trifluoromethylphenyl)-3-methyl-5-[1-di(2-cyanophenyl)amino-2,2,2-trichloroethyl]imino-1,3-diazolidine-2,4-dione;

1-(3-trifluoromethylphenyl)-3-methyl-5-[1-di(2'-trifluoromethylphenyl)amino-2,2,2-trichloroethyl]imino-1,3-diazolidine-2,4-dione; and 1-(3-trifluoromethylphenyl)-3-methyl-5-(1-2'-naphthylamino-2,2,2-trichloroethyl)imino-1,3-diazolidine-2,4-dione;

Similarly, by following the same procedure but replacing 1-(3-trifluoromethylphenyl)-3-methyl-5-(1,2,2,2-tetrachloroethyl)imino-1,3-diazolidine-1,4-dione with 1-(3-trifluoromethylphenyl)-3-ethyl-5-(1,2,2,2-tetrachloroethyl)imino-1,3-diazolidine-2,4-dione;

1-(3-trifluoromethylphenyl)-3-prop-2'-enyl-5-(1,2,2,2-tetrachloroethyl)imino-1,3-diazolidine-2,4-dione;

1-(3-trifluoromethylphenyl)-3-but-3'-ynyl-5-(1,2,2,2-tetrachloroethyl)imino-1,3-diazolidine-2,4-dione;

1-(3-trifluoromethylphenyl)-3-cyclohexyl-5-(1,2,2,2-tetrachloroethyl)imino-1,3-diazolidine-2,4-dione; and 1-(3-trifluoromethylphenyl)-3-methoxymethylene-5-(1,2,2,2-tetrachloroethyl)imino-1,3-diazolidine-2,4-dione, the corresponding 3-ethyl; 3-prop-2-enyl; 3-but-3-ynyl; 3-cyclohexyl and methoxymethylene analogs of each of the above-named compounds are respectively prepared.

Similarly the reverse 1-position-3-position isomers of each of the above prepared compounds are prepared by using the corresponding position isomer of formula A as the starting material. For example by using 1-methyl-3-trifluoromethylphenyl-5-(1,2,2,2-tetrachloroethyl)imino-1,3-diazolidine-2,4-dione in place of 1-(3-trifluoromethylphenyl)-methyl-5-(1,2,2,2-tetrachloroethyl)imino-1,3-diazolidone the following compounds (as well as the other 1–3 position isomers of each of the above products) are prepared:

1-methyl-3-(3-trifluoromethylphenyl)-5-(1-2'fluorophenylamino-2,2,2-trichloroethyl)imino-1,3-diazolidine-2,4-dione;

1-methyl-3-(3-trifluoromethylphenyl)-5-(1-phenylamino-2,2,2-trichloroethyl)imino-1,3-diazolidine-2,4-dione;

1-methyl-3-(3-trifluoromethylphenyl)-5-(1-2',4'difluorophenylamino-2,2,2-trichloroethyl)imino-1,3-diazolidine-2,4-dione;

1-methyl-3-(3-trifluoromethylphenyl)-5-(1-4'-chlorophenylamino-2,2,2-trichloroethyl)imino-1,3-diazolidine-2,4-dione;

1-methyl-3-(3-trifluoromethylphenyl)-5-(1-3',4'-dibromophenylamino-2,2,2-trichloroethyl)imino-1,3-diazolidine-2,4-dione;

1-methyl-3-(3-trifluoromethylphenyl)-5-(1-methylamino-2,2,2-trichloroethyl)imino-1,3-diazolidine-2,4-dione;

1-methyl-3-(3-trifluoromethylphenyl)-5-(1-but-3'-ynylamino-2,2,2-trichloroethyl)imino-1,3-diazolidine-2,4-dione;

1-methyl-3-(3-trifluoromethylphenyl)-5-(1-4'-methoxyphenylamino-2,2,2-trichloroethyl)imino-1,3-diazolidine-2,4-dione;

1-methyl-3-(3-trifluoromethylphenyl)-5-(1-2'nitrophenylamino-2,2,2-trichloroethyl)imino-1,3-diazolidine-2,4-dione;

1-methyl-3-(3-trifluoromethylphenyl)-5-[1-(2'-methoxy-3'-fluoro-4'-trifluoromethyl)phenylamino-2,2,2-trichloroethyl)]imino-1,3-diazolidine-2,4-dione.

EXAMPLE 4

This example illustrates the preparation of additional compounds of Formula 1.

In this example 0.02 mol of 1-(2-fluorophenyl)-3-methyl-5-(1,2-dichloroethyl)imino-1,3-diazolidine-2,4-dione is dissolved in 20 ml of acetonitrile and then 0.02 of mol of 2-chloroaniline is added. After about 10 minutes, triethylamine is added to neutralize the byproduct HCl produced by the reaction. The mixture is stirred for five hours and 20 ml of ethyl ether is then added. The mixture is filtered and the filtrate evaporated under high vacuum affording 1-(2-fluorophenyl)-3-methyl-5-(1-2'chlorophenylamino-2-chloroethyl)imino-1,3-diazolidine-2,4-dione.

Similarly by following the same procedure but using the corresponding primary or secondary amine as starting materials in place of 2-chlorophenylamine (i.e., 2-chloroaniline), the following compounds are respectively prepared:

1-(2-chlorophenyl)-3-methyl-5-(1-phenylamino-2-chloroethyl)imino-1,3-diazolidine-2,4-dione;

1-(2-chlorophenyl)-3-methyl-5-(1-3'-fluorophenylamino-2-chloroethyl)imino-1,3-diazolidine-2,4-dione;

1-(2-chlorophenyl)-3-methyl-5-(1-4'-fluorophenylamino-2-chloroethyl)imino-1,3-diazolidine-2,4-dione;

1-(2-chlorophenyl)-3-methyl-5-(1-2',4'-difluorophenylamino-2-chloroethyl)imino-1,3-diazolidine-2,4-dione;

1-(2-chlorophenyl)-3-methyl-5-(1-2',5'-difluorophenylamino-2-chloroethyl)imino-1,3-diazolidine-2,4-dione;

1-(2-chlorophenyl)-3-methyl-5-(1-2',3',4',5',6'-pentafluorophenylamino-2-chloroethyl)imino-1,3-diazolidine-2,4-dione;

1-(2-chlorophenyl)-3-methyl-5-(1-2'-fluorophenylamino-2-chloroethyl)imino-1,3-diazolidine-2,4-dione;

1-(2-chlorophenyl)-3-methyl-5-(1-4'-chlorophenylamino-2-chloroethyl)imino-1,3-diazolidine-2,4-dione;

1-(2-chlorophenyl)-3-methyl-5-(1-2',4'-dichlorophenylamino-2-chloroethyl)imino-1,3-diazolidine-2,4-dione;

1-(2-chlorophenyl)-3-methyl-5-(1-3',4'-dichlorophenylamino-2-chloroethyl)imino-1,3-diazolidine-2,4-dione;

1-(2-chlorophenyl)-3-methyl-5-(1-2'-bromophenylamino-2-chloroethyl)imino-1,3-diazolidine-2,4-dione;

1-(2-chlorophenyl)-3-methyl-5-(1-3',4'-dibromophenylamino-2-chloroethyl)imino-1,3-diazolidine-2,4-dione;

1-(2-chlorophenyl)-3-methyl-5-(1-3'-butylthiophenylamino-2-chloroethyl)imino-1,3-diazolidine-2,4-dione;

1-(2-chlorophenyl)-3-methyl-5-[1-(2-fluoro-3-bromo-4-chloro)phenylamino-2,2,2-trichloroethyl)]-2-chloroethyl)imino-1,3-diazolidine-2,4-dione;

1-(2-chlorophenyl)-3-methyl-5-(1-methylamino-2-chloroethyl)imino-1,3-diazolidine-2,4-dione;

1-(2-chlorophenyl)-3-methyl-5-(1-dimethylamino-2-chloroethyl)imino-1,3-diazolidine-2,4-dione;

1-(2-chlorophenyl)-3-methyl-5-(1-t-butylamino-2-chloroethyl)imino-1,3-diazolidine-2,4-dione;

1-(2-chlorophenyl)-3-methyl-5-(1-prop-2'-enylamino-2-chloroethyl)imino-1,3-diazolidine-2,4-dione;

1-(2-chlorophenyl)-3-methyl-5-(1-but-3'-ynylamino-2-chloroethyl)imino-1,3-diazolidine-2,4-dione;

1-(2-chlorophenyl)-3-methyl-5-(1-cyclopentylamino-2-chloroethyl)imino-1,3-diazolidine-2,4-dione;

1-(2-chlorophenyl)-3-methyl-5-(1-2'-methylphenylamino-2-chloroethyl)imino-1,3-diazolidine-2,4-dione;

1-(2-chlorophenyl)-3-methyl-5-(1-3'-propylphenylamino-2-chloroethyl)imino-1,3-diazolidine-2,4-dione;

1-(2-chlorophenyl)-3-methyl-5-(1-4'-t-butylphenylamino-2-chloroethyl)imino-1,3-diazolidine-2,4-dione;

1-(2-chlorophenyl)-3-methyl-5-(1-4'-methoxyphenylamino-2-chloroethyl)imino-1,3-diazolidine-2,4-dione;

1-(2-fluorophenyl)-3-methyl-5-(1-3'-isopropoxyphenylamino-2-chloroethyl)imino-1,3-diazolidine-2,4-dione;

1-(2-chlorophenyl)-3-methyl-5-(1-2',4'-dimethoxylphenylamino-2-chloroethyl)imino-1,3-diazolidine-2,4-dione;

1-(2-chlorophenyl)-3-methyl-5-(1-2'-nitrophenylamino-2-chloroethyl)imino-1,3-diazolidine-2,4-dione;

1-(2-chlorophenyl)-3-methyl-5-(1-2'-cyanophenylamino-2-chloroethyl)imino-1,3-diazolidine-2,4-dione;

1-(2-chlorophenyl)-3-methyl-5-(1-2'-trifluoromethylphenylamino-2-chloroethyl)imino-1,3-diazolidine-2,4-dione;

1-(2-chlorophenyl)-3-methyl-5-(1-4'-trifluoromethylphenylamino-2-chloroethyl)imino-1,3-diazolidine-2,4-dione;

1-(2-chlorophenyl)-3-methyl-5-(1-2',4'-ditrifluoromethylphenylamino-2-chloroethyl)amino-1,3-diazolidine-2,4-dione;

1-(2-chlorophenyl)-3-methyl-5-[1-(2'-methoxy-3'-fluoro-4'-trifluoromethyl)phenylamino-2-chloroethyl)]-imino-1,3-diazolidine-2,4-dione;

1-(2-chlorophenyl)-3-methyl-5-(1-diphenylamino-2-chloroethyl)imino-1,3-diazolidine-2,4-dione;

1-(2-chlorophenyl)-3-methyl-5-[1-(N-methyl-2'-fluorophenyl)amino-2-chloroethyl]imino-1,3-diazolidine-2,4-dione;

1-(2-chlorophenyl)-3-methyl-5-[1-di(4-fluorophenyl)amino-2-chloroethyl]imino-1,3-diazolidine-2,4-dione;

1-(2-chlorophenyl)-3-methyl-5-[1-(N-methyl-N-2,4-difluorophenyl)amino-2-chloroethyl]imino-1,3-diazolidine-2,4-dione;

1-(2-chlorophenyl)-3-methyl-5-[1-N-methyl-N-2-chlorophenyl)amino-2-chloroethyl]imino-1,3-diazolidine-2,4-dione;

1-(2-chlorophenyl)-3-methyl-5-[1-di(4-chlorophenyl)amino-2-chloroethyl]imino-1,3-diazolidine-2,4-dione;

1-(2-chlorophenyl)-3-methyl-5-[1-(N-methyl-N-2,4-dichlorophenyl)amino-2-chloroethyl]imino-1,3-diazolidine-2,4-dione;

1-(2-chlorophenyl)-3-methyl-5-[1-di(2-bromophenyl)amino-2-chloroethyl]imino-1,3-diazolidine-2,4-dione;

1-(2-chlorophenyl)-3-methyl-5-[1-di(2-methylthiophenyl)amino-2-chloroethyl]imino-1,3-diazolidine-2,4-dione;

1-(2-chlorophenyl)-3-methyl-5-(1-N-piperidinyl-2-chloroethyl)-imino-1,3-diazolidine-2,4-dione;

1-(2-chlorophenyl)-3-methyl-5-(1-pyrrolidinyl-2-chloroethyl)imino-1,3-diazolidine-2,4-dione;

1-(2-chlorophenyl)-3-methyl-5-(1-N-morpholinyl-2-chloroethyl)imino-1,3-diazolidine-2,4-dione;

1-(2-chlorophenyl)-3-methyl-5-(1-t-butylamino-2-chloroethyl)imino-1,3-diazolidine-2,4-dione;

1-(2-chlorophenyl)-3-methyl-5-[1-N-ethyl-N-prop-2'-enyl)amino-2-chloroethyl]imino-1,3-diazolidine-2,4-dione;

1-(2-chlorophenyl)-3-methyl-5-[1-(N-2-chlorophenyl-N-but-3'-ynyl)amino-2-chloro-ethyl]imino-1,3-diazolidine-2,4-dione;

1-(2-chlorophenyl)-3-methyl-5-[1-(N-2,4-dichlorophenyl-N-cyclopentyl)amino-2-chloroethyl]imino-1,3-diazolidine-2,4-dione;

1-(2-chlorophenyl)-3-methyl-5-(1-1'-naphthylamino-2-chloroethyl)imino-1,3-diazolidine-2,4-dione;

1-(2-chlorophenyl)-3-methyl-5-[1-di(2-methoxyphenyl)amino-2-chloroethyl]imino-1,3-diazolidine-2,4-dione;

1-(2-chlorophenyl)-3-methyl-5-[1-di(2-nitrophenyl)amino-2-chloroethyl]imino-1,3-diazolidine-2,4-dione;

1-(2-chlorophenyl)-3-methyl-5-[1-di(2',4'-dicyanophenyl)amino-2-chloroethyl]imino-1,3-diazolidine-2,4-dione; and 1-(2-chlorophenyl)-3-methyl-5-[1-(N-2,4-dichlorophenyl-N-trifluoromethyl-phenyl)amino-2-chloroethyl]imino-1,3-diazolidine-2,4-dione;

Similarly, by following the same procedure but replacing 1-2-chlorophenyl)-3-methyl-5-(1,2-dichloroethyl)imino-1,3-diazolidine-1,4-dione with 1-2-(chlorophenyl)-3-ethyl-5-(1,2-dichloroethyl-)imino1,3-diazolidine-2,4-dione;
1-(2-chlorophenyl)-3-prop-2'-enyl-5-(1,2-dichloroethyl-)imino-1,3-diazolidine-2,4-dione;
1-(2-chlorophenyl)-3-but-3'-ynyl-5-(1,2-dichloroethyl-)imino-1,3-diazolidine-2,4-dione;
1-(2-chlorophenyl)-3-cyclohexyl-5-(1,2-dichloroethyl-)imino-1,3-diazolidine-2,4-dione; and
1-(2-chlorophenyl)-3-methoxymethylene-5-(1,2-dichloroethyl)imino-1,3-diazolidine-2,4-dione, the corresponding 3-ethyl; 3-prop-2-enyl; 3-but-3-ynyl; 3-cyclohexyl and methoxymethylene analogs of each of the above-named compounds are respectively prepared.

Similarly the reverse 1-position-3-position isomers of each of the above prepared compounds are prepared by using the corresponding position isomer of formula A as the starting material. For example, by using 1-methyl-3-(2-chlorophenyl)-5-(1,2-dichloroethyl)imino-1,3-diazolidine-2,4-dione in place of 1-(2-chlorophenyl-3-methyl-5-(1,2-dichloroethyl)imino-1,3-diazolidine the following compounds (as well as the other 1–3 positions isomers of each of the above products are prepared:

1-methyl-3-(2-chlorophenyl)-5-(1-2'-chloro-phenylamino-2-chloroethyl)imino-1,3-diazolidine-2,4-dione;
1-methyl-3-(2-chlorophenyl)-5-(1-phenylamino-2-chloroethyl)imino-1,3-diazolidine-2,4-dione;
1-methyl-3-(2-chlorophenyl)-5-(difluorophenylamino-2-chloroethyl)imino-1,3-diazolidine-2,4-dione;
1-methyl-3-(2-chlorophenyl)-5-(1-3',4'-dichloro-phenylamino-2-chloroethyl)imino-1,3-diazolidine-2,4-dione;
1-methyl-3-(2-chlorophenyl)-5-(1-methylamino-2-chloroethyl)imino-1,3-diazolidine-2,4-dione;
1-methyl-3-(2-chlorophenyl)-5-(1-cyclopentylamino-2-chloroethyl)imino-1,3-diazolidine-2,4-dione;
1-methyl-3-(2-chlorophenyl)-5-(1-3'-isopropoxy-phenylamino-2-chloroethyl)imino-1,3-diazolidine-2,4-dione;
1-methyl-3-(2-chlorophenyl)-5-(1-4'-trifluoromethyl-phenylamino-2-chloroethyl)imino-1,3-diazolidine-2,4-dione.

EXAMPLE 5

This example illustrates the preparation of further compounds of Formula 1.

In this example 0.02 mol of 1-(2-fluorophenyl)-3-methyl-5-(1,2,3,3,3-pentachloropropyl)imino-1,3-diazolidine-2,4-dione is dissolved in 20 ml of acetonitrile and then 0.02 of mol of 2-fluoroaniline is added. After about 10 minutes, triethylamine is added to neutralize the byproduct HCl produced by the reaction. The mixture is stirred for five hours and 20 ml of ethyl ether is then added. The mixture is filtered and the filtrate evaporated under high vacuum affording 1-(2-fluoro-phenyl)-3-methyl-5-(1-2'-fluorophenylamino-2,3,3,3-tetrachloropropyl)imino-1,3-diazolidine-2,4-dione.

Following the same procedure but using the corresponding primary or secondary amines as starting materials in place of 2-fluorophenylamine, the following compounds are respectively prepared:

1-(2-fluorophenyl)-3-methyl-5-(1-phenylamino-2,3,3,3-tetrachloropropyl)imino-1,3-diazolidine-2,4-dione;
1-(2-fluorophenyl)-3-methyl-5-(1-3'-fluoro-phenylamino-2,3,3,3-tetrachloropropyl)imino-1,3-diazolidine-2,4-dione;
1-(2-fluorophenyl)-3-methyl-5-(1-4'-fluoro-phenylamino-2,3,3,3-tetrachloropropyl)imino-1,3-diazolidine-2,4-dione;
1-(2-fluorophenyl)-3-methyl-5-(1-2',4'-difluoro-phenylamino-2,3,3,3-tetrachloropropyl)imino-1,3-diazolidine-2,4-dione;
1-(2-fluorophenyl)-3-methyl-5-(1-2',5'-difluoro-phenylamino-2,3,3,3-tetrachloropropyl)imino-1,3-diazolidine-2,4-dione;
1-(2-fluorophenyl)-3-methyl-5-(1-2',3',4',5',6'-pentafluorophenylamino-2,3,3,3-tetrachloropropyl)imino-1,3-diazolidine-2,4-dione;
1-(2-fluorophenyl)-3-methyl-5-(1-anthr-2'-ylamino-2,3,3,3-tetrachloropropyl)imino-1,3-diazolidine-2,4-dione;
1-(2-fluorophenyl)-3-methyl-5-(1-phenanthr-2'-ylamino-2,3,3,3-tetrachloropropyl)imino-1,3-diazolidine-2,4-dione;
1-(2-fluorophenyl)-3-methyl-5-(1-2'-chloro-phenylamino-2,3,3,3-tetrachloropropyl)imino-1,3-diazolidine-2,4-dione;
1-(2-fluorophenyl)-3-methyl-5-(1-4'-chloro-phenylamino-2,3,3,3-tetrachloropropyl)imino-1,3-diazolidine-2,4-dione;
1-(2-fluorophenyl)-3-methyl-5-(1-2'4'-dichloro-phenylamino-2,3,3,3-tetrachloropropyl)imino-1,3-diazolidine-2,4-dione;
1-(2-fluorophenyl)-3-methyl-5-(1-3'4'-dichloro-phenylamino-2,3,3,3-tetrachloropropyl)imino-1,3-diazolidine-2,4-dione;
1-(2-fluorophenyl)-3-methyl-5-(1-2'-bromo-phenylamino-2,3,3,3-tetrachloropropyl)imino-1,3-diazolidine-2,4-dione;
1-(2-fluorophenyl)-3-methyl-5-(1-3'4'-dibromo-phenylamino-2,3,3,3-tetrachloropropyl)imino-1,3-diazolidine-2,4-dione;
1-(2-fluorophenyl)-3-methyl-5-(1-3'-methylsulfinyl-phenylamino-2,3,3,3-tetrachloropropyl)imino-1,3-diazolidine-2,4-dione;
1-(2-fluorophenyl)-3-methyl-5-(1-2'4'-methylthio-phenylamino-2,3,3,3-tetrachloropropyl)imino-1,3-diazolidine-2,4-dione;
1-(2-fluorophenyl)-3-methyl-5-[1-(2-fluoro-3-bromo-4-chloro)phenylamino-2,2,2-trichloroethyl)]-2,3,3,3-tetrachloropropyl)imino-1,3-diazolidine-2,4-dione;
1-(2-fluorophenyl)-3-methyl-5-(1-methylamino-2,3,3,3-tetrachloropropyl)imino-1,3-diazolidine-2,4-dione;
1-(2-fluorophenyl)-3-methyl-5-(1-dimethylamino-2,3,3,3-tetrachloropropyl)imino-1,3-diazolidine-2,4-dione;
1-(2-fluorophenyl)-3-methyl-5-(1-t-butylamino-2,3,3,3-tetrachloropropyl)imino-1,3-diazolidine-2,4-dione;
1-(2-fluorophenyl)-3-methyl-5-(1-prop-2'-enylamino-2,3,3,3-tetrachloropropyl)imino-1,3-diazolidine-2,4-dione;
1-(2-fluorophenyl)-3-methyl-5-(1-but-3'-ynylamino-2,3,3,3-tetrachloropropyl)imino-1,3-diazolidine-2,4-dione;
1-(2-fluorophenyl)-3-methyl-5-(1-cyclopentylamino-2,3,3,3-tetrachloropropyl)imino-1,3-diazolidine-2,4-dione;
1-(2-fluorophenyl)-3-methyl-5-(1-2'-methyl-phenylamino-2,3,3,3-tetrachloropropyl)imino-1,3-diazolidine-2,4-dione;

1-(2-fluorophenyl)-3-methyl-5-(1-3'-propyl-phenylamino-2,3,3,3-tetrachloropropyl)imino-1,3-diazolidine-2,4-dione;

1-(2-fluorophenyl)-3-methyl-5-(1-4'-t-butyl-phenylamino-2,3,3,3-tetrachloropropyl)imino-1,3-diazolidine-2,4-dione;

1-(2-fluorophenyl)-3-methyl-5-(1-4'-methoxy-phenylamino-2,3,3,3-tetrachloropropyl)imino-1,3-diazolidine-2,4-dione;

1-(2-fluorophenyl)-3-methyl-5-(1-3'-isopropoxy-phenylamino-2,3,3,3-tetrachloropropyl)imino-1,3-diazolidine-2,4-dione;

1-(2-fluorophenyl)-3-methyl-5-(1-2',4'-dimethoxyl-phenylamino-2,3,3,3-tetrachloropropyl)imino-1,3-diazolidine-2,4-dione;

1-(2-fluorophenyl)-3-methyl-5-(1-2'-nitrophenylamino-2,3,3,3-tetrachloropropyl)imino-1,3-diazolidine-2,4-dione;

1-(2-fluorophenyl)-3-methyl-5-(1-2'-cyano-phenylamino-2,3,3,3-tetrachloropropyl)imino-1,3-diazolidine-2,4-dione;

1-(2-fluorophenyl)-3-methyl-5-(1-2'-trifluoromethyl-phenylamino-2,3,3,3-tetrachloropropyl)imino-1,3-diazolidine-2,4-dione;

1-(2-fluorophenyl)-3-methyl-5-(1-4'-trifluoromethyl-phenylamino-2,3,3,3-tetrachloropropyl)imino-1,3-diazolidine-2,4-dione;

1-(2-fluorophenyl)-3-methyl-5-[1-(2-methoxy-3-fluoro-4-trifluoromethylphenyl)amino-2,3,3,3-tetrachloropropyl)]-imino and 1-3'4'-ditrifluoromethylamino;

1-(2-fluorophenyl)-3-methyl-5-[1-di(2,4-difluorophenyl)amino-2,3,3,3-tetrachloropropyl]imino-1,3-diazolidine-2,4-dione;

1-(2-fluorophenyl)-3-methyl-5-[1-di(3,4-difluorophenyl)amino-2,3,3,3-tetrachloropropyl]imino-1,3-diazolidine-2,4-dione;

1-(2-fluorophenyl)-3-methyl-5-[1-(N-methyl-N-2,3,4,5,6-pentafluorophenyl)amino-2,3,3,3-tetrachloropropyl]imino-1,3-diazolidine-2,4-dione;

1-(2-fluorophenyl)-3-methyl-5-[1-(N-cyclohexyl-N-2'-chlorophenyl)amino-2,3,3,3-tetrachloropropyl]imino-1,3-diazolidine-2,4-dione;

1-(2-fluorophenyl)-3-methyl-5-[1-di(4-chlorophenyl)amino-2,3,3,3-tetrachloropropyl]imino-1,3-diazolidine-2,4-dione;

1-(2-fluorophenyl)-3-methyl-5-[1-(N-methyl-N-2,4-dichlorophenyl)amino-2,3,3,3-tetrachloropropyl]imino-1,3-diazolidine-2,4-dione;

1-(2-fluorophenyl)-3-methyl-5-[1-di(3,4-dichlorophenyl)amino-2,3,3,3-tetrachloropropyl]imino-1,3-diazolidine-2,4-dione;

1-(2-fluorophenyl)-3-methyl-5-[1-di(2-bromophenyl)amino-2,3,3,3-tetrachloropropyl]imino-1,3-diazolidine-2,4-dione;

1-(2-fluorophenyl)-3-methyl-5-[1-(N-phenyl-N-3,4-dibromophenyl)amino-2,3,3,3-tetrachloropropyl]imino-1,3-diazolidine-2,4-dione;

1-(2-fluorophenyl)-3-methyl-5-[1-di(3-methylsulfinyl-phenyl)amino-2,3,3,3-tetrachloropropyl]imino-1,3-diazolidine-2,4-dione;

1-(2-fluorophenyl)-3-methyl-5-[1-(N-methyl-N-4-t-butylsulfonylphenyl)amino-2,3,3,3-tetrachloropropyl]imino-1,3-diazolidine-2,4-dione;

1-(2-fluorophenyl)-3-methyl-5-[1-di(2-fluoro-3-bromo-4-chlorophenyl)amino-2,3,3,3-tetrachloropropyl]imino-1,3-diazolidine-2,4-dione;

1-(2-fluorophenyl)-3-methyl-5-(1-methylthioamino-2,3,3,3-tetrachloropropyl)imino-1,3-diazolidine-2,4-dione;

1-(2-fluorophenyl)-3-methyl-5-(1-N,N-dimethylthioamino-2,3,3,3-tetrachloropropyl)imino-1,3-diazolidine-2,4-dione;

1-(2-fluorophenyl)-3-methyl-5-(1-di-t-butylamino-2,3,3,3-tetrachloropropyl)imino-1,3-diazolidine-2,4-dione;

1-(2-fluorophenyl)-3-methyl-5-(1-diphenylamino-2,3,3,3-tetrachloropropyl)imino-1,3-diazolidine-2,4-dione;

1-(2-fluorophenyl)-3-methyl-5-[1-di(prop-2-enyl)amino-2,3,3,3-tetrachloropropyl]imino-1,3-diazolidine-2,4-dione;

1-(2-fluorophenyl)-3-methyl-5-(1-dicyclopentylamino-2,3,3,3-tetrachloropropyl)imino-1,3-diazolidine-2,4-dione;

1-(2-fluorophenyl)-3-methyl-5-[1-di(2-methylphenyl)amino-2,3,3,3-tetrachloropropyl]imino-1,3-diazolidine-2,4-dione;

1-(2-fluorophenyl)-3-methyl-5-[1-(N-4-chlorophenyl-4-methoxyphenyl)amino-2,3,3,3-tetrachloropropyl]imino-1,3-diazolidine-2,4-dione;

1-(2-fluorophenyl)-3-methyl-5-(1-N-piperildinyl-2,3,3,3-tetrachloropropyl)imino-1,3-diazolidine-2,4-dione;

1-(2-fluorophenyl)-3-methyl-5-(1-N-pyrrolidinyl-2,3,3,3-tetrachloropropyl)imino-1,3-diazolidine-2,4-dione;

1-(2-fluorophenyl)-3-methyl-5-(1-N-morpholinyl-2,3,3,3-tetrachloropropyl)imino-1,3-diazolidine-2,4-dione;

1-(2-fluorophenyl)-3-methyl-5-[1-di(2-cyanophenyl)amino-2,3,3,3-tetrachloropropyl]imino-1,3-diazolidine-2,4-dione;

1-(2-fluorophenyl)-3-methyl-5-[1-(N-methyl-N-2-trifluoromethylphenyl)amino-2,3,3,3-tetrachloropropyl]imino-1,3-diazolidine-2,4-dione; and 1-(2-fluorophenyl)-3-methyl-5(1-naphthylamino-2,3,3,3-tetrachloropropyl)amino-1,3-diazolidine-2,4-dione.

Similarly, by following the same procedure but replacing 1-(2-fluorophenyl)-3-methyl-5-(1,2,3,3,3-pentachloropropyl)imino-1,3-diazolidine-1,4-dione with 1-(2-fluorophenyl)-3-ethyl-5-(1,2,3,3,3-pentachloropropyl)imino-1,3-diazolidine-2,4-dione;

1-(2-fluorophenyl)-3-prop-2-enyl-5-(1,2,3,3,3-pentachloropropyl)imino-1,3-diazolidine-2,4-dione;

1-(2-fluorophenyl)-3-but-3'-ynyl-5-(1,2,3,3,3-pentachloropropyl)imino-1,3-diazolidine-2,4-dione;

1-(2-fluorophenyl)-3-cyclohexyl-5-(1,2,3,3,3-pentachloropropyl)imino-1,3-diazolidine-2,4-dione; and 1-(2-fluorophenyl)-3-methoxymethylene-5-(1,2,3,3,3-pentachloropropyl)imino-1,3-diazolidine-2,4-dione, the corresponding 3-ethyl; 3-prop-2-enyl; 3-but-3-ynyl; 3-cyclohexyl and methoxymethylene analogs of each of the above-named compounds are respectively prepared.

Similarly the reverse 1-position-3-position isomers of each of the above prepared compounds are prepared by using the corresponding position isomer of formula A as the starting material. For example by using 1-methyl-3-(2-fluorophenyl)-5-(1,2,3,3,3-pentachloropropyl)imino-1,3-diazolidine-2,4-dione in place of 1-(2-fluorophenyl)-3-methyl-5-(1,2,3,3,3-pentachloropropyl)imino-1,3-diazolidine the following compounds (as well as the other position isomers of the above products) are prepared:

1-methyl-3-(2-fluorophenyl)-5-(1-2'-fluoro-
  phenylamino-2,3,3,3-tetrachloropropyl)imino-1,3-
  diazolidine-2,4-dione;
1-methyl-3-(2-fluorophenyl)-5-(phenylamino-2,3,3,3-
  tetrachloropropyl)imino-1,3-diazolidine-2,4-dione;
1-methyl-3-(2-fluorophenyl)-5-(1-2',3',4',5',6'-penta-
  fluorophenylamino-2,3,3,3-tetrachloropropyl)imino-
  1,3-diazolidine-2,4-dione;
1-methyl-3-(2-fluorophenyl)-5-(1-2',4'-dichloro-
  phenylamino-2,3,3,3-tetrachloropropyl)imino-1,3-
  diazolidine-2,4-dione;
1-methyl-3-(2-fluorophenyl)-5-[1-(2-fluoro-3-bromo-4-
  chlorophenyl)amino-2,3,3,3-tetrachloropropyl-
  ]imino-1,3-diazolidine-2,4-dione;
1-methyl-3-(2-fluorophenyl)-5-(1-cyclopentylamino-
  2,3,3,3-terachloropropyl)imino-1,3-diazolidine-2,4-
  dione;
1-methyl-3-(2-fluorophenyl)-5-(1-2',4'-dimethoxyl-
  phenylamino-2,3,3,3-tetrachloropropyl)imino-1,3-
  diazolidine-2,4-dione.

EXAMPLE 6

This example illustrates the preparation of further compounds of Formula 1.

In this example 0.02 mol of 1-(2-fluorophenyl)-3-methyl-5-(1,3-dichloro-2,2-dibromopropyl)imino-1,3-diazolidine-2,4-dione is dissolved in 20 ml of acetonitrile and then 0.02 of mol of 2-bromoaniline is added. After about 10 minutes, triethylamine is added to neutralize the byproduct HCl produced by the reaction. The mixture is stirred for five hours and 20 ml of ethyl ether is then added. The mixture is filtered and the filtrate evaporated under high vacuum affording 1-(2-fluorophenyl)-3-methyl-5-(1-2'-bromophenylamino-2,2,-dibromo-3-chloropropyl)imino-1,3-diazolidine-2,4-dione.

Following the same procedure but using the corresponding primary or secondary amines as starting materials in place of 2-fluorophenylamine, the following compounds are respectively prepared:

1-(2-fluorophenyl)-3-methyl-5-(1-phenylamino-2,2-
  dibromo-3-chloropropyl)imino-1,3-diazolidine-2,4-
  dione;
1-(2-fluorophenyl)-3-methyl-5-(1-3'-fluoro-
  phenylamino-2,2-dibromo-3-chloropropyl)imino-1,3-
  diazolidine-2,4-dione;
1-(2-fluorophenyl)-3-methyl-5-(1-4'-fluoro-
  phenylamino-2,2-dibromo-3-chloropropyl)imino-1,3-
  diazolidine-2,4-dione;
1-(2-fluorophenyl)-3-methyl-5-(1-2',4'-difluoro-
  phenylamino-2,2-dibromo-3-chloropropyl)imino-1,3-
  diazolidine-2,4-dione;
1-(2-fluorophenyl)-3-methyl-5-(1-2',4'-difluoro-
  phenylamino-2,2-dibromo-3-chloropropyl)imino-1,3-
  diazolidine-2,4-dione;
1-(2-fluorophenyl)-3-methyl-5-difluorophenylamino-
  2,2-dibromo-3-chloropropyl)imino-1,3-diazolidine-
  2,4-dione;
1-(2-fluorophenyl)-3-methyl-5-(1-2',3',4',5',6'-penta-
  fluorophenylamino-2,2-dibromo-3-chloropropyl-
  )imino-1,3-diazolidine-2,4-dione;
1-(2-fluorophenyl)-3-methyl-5-(1-2'-chloro-
  phenylamino-2,2-dibromo-3-chloropropyl)imino-1,3-
  diazolidine-2,4-dione;
1-(2-fluorophenyl)-3-methyl-5-(1-4'-chloro-
  phenylamino-2,2-dibromo-3-chloropropyl)imino-1,3-
  diazolidine-2,4-dione;
1-(2-fluorophenyl)-3-methyl-5-(1-2'4'-dichloro-
  phenylamino-2,2-dibromo-3-chloropropyl)imino-1,3-
  diazolidine-2,4-dione;
1-(2-fluorophenyl)-3-methyl-5-(1-3'4'-dichloro-
  phenylamino-2,2-dibromo-3-chloropropyl)imino-1,3-
  diazolidine-2,4-dione;
1-(2-fluorophenyl)-3-methyl-5-(1-2'-fluoro-
  phenylamino-2,2-dibromo-3-chloropropyl)imino-1,3-
  diazolidine-2,4-dione;
1-(2-fluorophenyl)-3-methyl-5-(1-3'4'-dibromo-
  phenylamino-2,2-dibromo-3-chloropropyl)imino-1,3-
  diazolidine-2,4-dione;
1-(2-fluorophenyl)-3-methyl-5-(1-2'-ethylsulfonyl-
  phenylamino-2,2-dibromo-3-chloropropyl)imino-1,3-
  diazolidine-2,4-dione;
1-(2-fluorophenyl)-3-methyl-5-(1-2'4'-dimethylthio-
  phenylamino-2,2-dibromo-3-chloropropyl)imino-1,3-
  diazolidine-2,4-dione;
1-(2-fluorophenyl)-3-methyl-5-[1-(2-fluoro-3-bromo-4-
  chloro)phenylamino-2,2,2-trichloroethyl)]-2,2-
  dibromo-3-chloropropyl)imino-1,3-diazolidine-2,4-
  dione;
1-(2-fluorophenyl)-3-methyl-5-(1-methylamino-2,2-
  dibromo-3-chloropropyl)imino-1,3-diazolidine-2,4-
  dione;
1-(2-fluorophenyl)-3-methyl-5-(1-dimethylamino-2,2-
  dibromo-3-chloropropyl)imino-1,3-diazolidine-2,4-
  dione;
1-(2-fluorophenyl)-3-methyl-5-(1-t-butylamino-2,2-
  dibromo-3-chloropropyl)imino-1,3-diazolidine-2,4-
  dione;
1-(2-fluorophenyl)-3-methyl-5-(1-prop-2'-enylamino-
  2,2-dibromo-3-chloropropyl)imino-1,3-diazolidine-
  2,4-dione;
1-(2-fluorophenyl)-3-methyl-5-(1-but-3'-ynylamino-2,2-
  dibromo-3-chloropropyl)imino-1,3-diazolidine-2,4-
  dione;
1-(2-fluorophenyl)-3-methyl-5-(1-cyclopentylamino-
  2,2-dibromo-3-chloropropyl)imino-1,3-diazolidine-
  2,4-dione;
1-(2-fluorophenyl)-3-methyl-5-(1-2'-methyl-
  phenylamino-2,2-dibromo-3-chloropropyl)imino-1,3-
  diazolidine-2,4-dione;
1-(2-fluorophenyl)-3-methyl-5-(1-3'-propyl-
  phenylamino-2,2-dibromo-3-chloropropyl)imino-1,3-
  diazolidine-2,4-dione;
1-(2-fluorophenyl)-3-methyl-5-(1-4'-t-butyl-
  phenylamino-2,2-dibromo-3-chloropropyl)imino-1,3-
  diazolidine-2,4-dione;
1-(2-fluorophenyl)-3-methyl-5-(1-4'-methoxy-
  phenylamino-2,2-dibromo-3-chloropropyl)imino-1,3-
  diazolidine-2,4-dione;
1-(2-fluorophenyl)-3-methyl-5-(1-3'-isopropoxy-
  phenylamino-2,2-dibromo-3-chloropropyl)imino-1,3-
  diazolidine-2,4-dione;
1-(2-fluorophenyl)-3-methyl-5-(1-2',4'-dimethoxyl-
  phenylamino-2,2-dibromo-3-chloropropyl)imino-1,3-
  diazoline-2,4-dione;
1-(2-fluorophenyl)-3-methyl-5-(1-2'-nitrophenylamino-
  2,2-dibromo-3-chloropropyl)imino-1,3-diazolidine-
  2,4-dione;
1-(2-fluorophenyl)-3-methyl-5-(1-2'-cyano-
  phenylamino-2,2-dibromo-3-chloropropyl)imino-1,3-
  diazolidine-2,4-dione;
1-(2-fluorophenyl)-3-methyl-5-(1-2'-trifluoromethyl-
  phenylamino-2,2-dibromo-3-chloropropyl)imino-1,3-
  diazolidine-2,4-dione;

1-(2-fluorophenyl)-3-methyl-5-(1-4'-trifluoromethyl-
phenylamino-2,2-dibromo-3-chloropropyl)imino-1,3-
diazolidine-2,4-dione;

1-(2-fluorophenyl)-3-methyl-5-[1-(2'-methoxy-3'-fluoro-
4'-trifluoromethyl)phenylamino-2,2-dibromo-3-
chloropropyl)]imino-1,3-diazolidine-2,4-dione.

1-(2-fluorophenyl)-3-methyl-5-[1-di(2,4-difluorophenyl-
)amino-2,2-dibromo-3-chloropropyl]imino-1,3-
diazolidine-2,4-dione;

1-(2-fluorophenyl)-3-methyl-5-[1-(N-methyl-N-
2,3,4,5,6-pentafluorophenyl)amino-2,2-dibromo-3-
chloropropyl]imino-1,3-diazolidine-2,4-dione;

1-(2-fluorophenyl)-3-methyl-5-[1-di(4-chlorophenyl-
)amino-2,2-dibromo-3-chloropropyl]imino-1,3-
diazolidine-2,4-dione;

1-(2-fluorophenyl)-3-methyl-5-[1-di(3,4-dichloro-
phenyl)amino-2,2-dibromo-3-chloropropyl]imino-
1,3-diazolidine-2,4-dione;

1-(2-fluorophenyl)-3-methyl-5-[1-(N-phenyl-N-3,4-
dibromophenyl)amino-2,2-dibromo-3-chloropropyl-
]imino-1,3-diazolidine-2,4-dione;

1-(2-fluorophenyl)-3-methyl-5-[1-(N-methyl-N-4-t-
butylsulfonylphenyl)amino-2,2-dibromo-3-chloro-
propyl]imino-1,3-diazolidine-2,4-dione;

1-(2-fluorophenyl)-3-methyl-5-(1-methylthioamino-2,2-
dibromo-3-chloropropyl)imino-1,3-diazolidine-2,4-
dione;

1-(2-fluorophenyl)-3-methyl-5-(1-di-t-butylamino-2,2-
dibromo-3-chloropropyl)imino-1,3-diazolidine-2,4-
dione;

1-(2-fluorophenyl)-3-methyl-5-[1-di(prop-2-enyl)amino-
2,2-dibromo-3-chloropropyl]imino-1,3-diazolidine-
2,4-dione;

1-(2-fluorophenyl)-3-methyl-5-[1-di(2-methylphenyl-
)amino-2,2-dibromo-3-chloropropyl]imino-1,3-
diazolidine-2,4-dione;

1-(2-fluorophenyl)-3-methyl-5-(1-N-piperidinyl-2,2-
dibromo-3-chloropropyl)imino-1,3-diazolidine-2,4-
dione;

1-(2-fluorophenyl)-3-methyl-5-(1-N-morpholinyl-2,2-
dibromo-3-chloropropyl)imino-1,3-diazolidine-2,4-
dione;

1-(2-fluorophenyl)-3-methyl-5-[1-(N-methyl-N-2-tri-
fluoromethylphenylamino-2,2-dibromo-3-chloro-
propyl]imino-1,3-diazolidine-2,4-dione; and 1-(2-fluorophenyl)-3-methyl-5-(1-naphth-2'-ylamino-
2,2-dibromo-3-chloropropyl)imino-1,3-diazolidine-
2,4-dione.

Similarly, by following the same procedure but replacing 1-(2-fluorophenyl)-3-methyl-5-(amino-2,2-dibromo-1,3-dichloropropyl)imino-1,3-diazolidine-1,4-dione with 1-(2-fluorophenyl)-3-ethyl-5-(2,2-dibromo-1,3-dichloro-
propyl)imino-1,3-diazolidine-2,4-dione;

1-(2-fluorophenyl)-3-prop-2'-enyl-5-(2,2-dibromo-1,3-
dichloropropyl)imino-1,3-diazolidine-2,4-dione;

1-(2-fluorophenyl)-3-but-3-ynyl-5-(2,2-dibromo-1,3-
dichloropropyl)imino-1,3-diazolidine-2,4-dione;

1-(2-fluorophenyl)-3-cyclohexyl-5-(2,2-dibromo-1,3-
dichloropropyl)imino-1,3-diazolidine-2,4-dione; and 1-(2-fluorophenyl)-3-methoxymethylene-5-(2,2-
dibromo-1,3-dichloropropyl)imino-1,3-diazolidine-
2,4-dione, the corresponding 3-ethyl; 3-prop-2-enyl;
3-but-3-ynyl; 3-cyclohexyl and methoxymethylene
analogs of each of the above-named compounds are
respectively prepared.

Similarly the reverse 1-position-3-position isomers of
each of the above prepared compounds are prepared by
using the corresponding position isomer of formula A as
the starting lmaterial. For example by using 1-methyl-3-
fluorophenyl-5-(1,3-dichloro-2,2-dibromopropyl)imino-
1,3-diazolidine-2,4-dione in place of 1-(2-fluorophenyl)-
3-methyl-5-(1,3-dibromo-2,2-dibromopropyl)imino-1,3-
diazolidone the following compounds as well as the
other position isomers of the other products prepared
above) are prepared:

1-methyl-3-(2-fluorophenyl)-5-(1-2'-bromo-
phenylamino-2,2-dibromo-3-chloropropyl)imino-1,3-
diazolidine-2,4-dione;

1-methyl-3-(2-fluorophenyl)-5-(1-phenylamino-2,2-
dibromo-3-chloropropyl)imino-1,3-diazolidine-2,4-
dione;

1-methyl-3-(2-fluorophenyl)-5-(1-2',4'-difluoro-
phenylamino-2,2-dibromo-3-chloropropyl)imino-1,3-
diazolidine-2,4-dione;

1-methyl-3-(2-fluorophenyl)-5-(1-2'-chloro-
phenylamino-2,2-dibromo-3-chloropropyl)imino-1,3-
diazolidine-2,4-dione;

1-methyl-3-(2-fluorophenyl)-5-(1,2'-fluoro-
phenylamino-2,2-dibromo-3-chloropropyl)imino-1,3-
diazolidine-2,4-dione;

1-methyl-3-(2-fluorophenyl)-5-[1-(2-fluoro-3-bromo-4-
chlorophenyl)amino-2,2-dibromo-3-chloropropyl-
]imino-1,3-diazolidine-2,4-dione;

1-methyl-3-(2-fluorophenyl)-5-(1-prop-2'-enylamino-
2,2-dibromo-3-chloropropyl)imino-1,3-diazolidine-
2,4-dione;

1-methyl-3-(2-fluorophenyl)-5-(1-3'-propyl-
phenylamino-2,2-dibromo-3-chloropropyl)imino-1,3-
diazolidine-2,4-dione;

1-methyl-3-(2-fluorophenyl)-5-(1-2',4'-dimethoxyl-
phenylamino-2,2-dibromo-3-chloropropyl)imino-1,3-
diazolidine-2,4-dione;

1-methyl-3-(2-fluorophenyl)-5-(1-4'-trifluoromethyl-
phenylamino-2,2-dibromo-3-chloropropyl)imino-1,3-
diazolidine-2,4-dione.

EXAMPLE 7

This example illustrates the preparation of still further compounds of the invention.

In this example 0.02 mol of 1-(3,5-dichlorophenyl)-3-methyl-5-(1,2,2,2-tetrachloroethyl)imino-1,3-diazolidine-2,4-dione is dissolved in 20 ml of acetonitrile and then 0.02 of mol of 2,4-dichloroaniline is added. After about 10 minutes, triethylamine is added to nrutralize the byproduct HCl produced by the reaction. The mixture is stirred for five hours and 20 ml of ethyl ether is then added. The mixture is filtered and the filtrate evaporated under high vacuum affording 1-(3,5-dichlorophenyl)-3-methyl-5-(1-2',4'dichlorophenylamino-2,2,2-trichloroethyl)imino-1,3-diazolidine.

Similarly by following the same procedure but using the corresponding compounds of formula A as starting materials the following compounds are respectively prepared:

1-anthr-2'-yl-3-methyl-5-(1-2',4'-dichlorophenylamino-
2,2,2-trichloroethyl)imino-1,3-diazolidine-2,4-dione;

1-phenanthr-2'yl-3-methyl-5-(1-2',4'-dichlorophenyl-
2,2,2-trichloroethyl)imino-1,3-diazolidine-2,4-dione;

1-(2,4-difluorophenyl)-3-methyl-5-(1-2',4'-dichloro-
phenylamino-2,2,2-trichloroethyl)imino-1,3-diazoli-
dine-2,4-dione;

1-(2,3,4,5,6-pentachlorophenyl)-3-methyl-5-(1-2',4'-
dichlorophenylamino-2,2,2-trichloroethyl)imino-1,3-
diazolidine-2,4-dione;

1-(2-bromophenyl)-3-methyl-5-(1-2',4'-dichlorophenylamino-2,2,2-trichloroethyl)imino-1,3-diazolidine-2,4-dione;

1-(2,4-dibromophenyl)-3-methyl-5-(1-2',4'-dichlorophenylamino-2,2,2-trichloroethyl)imino-1,3-diazolidine-2,4-dione;

1-(2-methylthiophenyl)-3-methyl-5-(1-2',4'-dichlorophenylamino-2,2,2-trichloroethyl)imino-1,3-diazolidine-2,4-dione;

1-(3-ethylsulfinylphenyl)-3-methyl-5-(1-2',4'-dichlorophenylamino-2,2,2-trichloroethyl)imino-1,3-diazolidine-2,4-dione;

1-(2,4-dimethylsulfonylphenyl)-3-methyl-5-(1-2',4'-dichlorophenylamino-2,2,2-trichloroethyl)imino-1,3-diazolidine-2,4-dione;

1-(2-methylaminophenyl)-3-methyl-5-(1-2',4'-dichlorophenylamino-2,2,2-trichloroethyl)imino-1,3-diazolidine-2,4-dione;

1-(2,4-dimethylaminophenyl)-3-methyl-5-(1-2',4'-dichlorophenylamino-2,2,2-trichloroethyl)imino-1,3-diazolidine-2,4-dione;

1-(2-isopropylaminophenyl)-3-methyl-5-(1-2',4'-dichlorophenylamino-2,2,2-trichloroethyl)imino-1,3-diazolidine-2,4-dione;

1-(2-methoxyphenyl)-3-methyl-5-(1-2',4'-dichlorophenylamino-2,2,2-trichloroethyl)imino-1,3-diazolidine-2,4-dione;

1-(2,4-dicyanophenyl)-3-methyl-5-(1-2',4'-dichlorophenylamino-2,2,2-trichloroethyl)imino-1,3-diazolidine-2,4-dione;

1-(4-nitrophenyl)-3-methyl-5-(1-2',4'-dichlorophenylamino-2,2,2-trichloroethyl)imino-1,3-diazolidine-2,4-dione;

1-(2,4-ditrifluoromethylphenyl)-3-methyl-5-(1-2',4'-dichlorophenylamino-2,2,2-trichloroethyl)imino-1,3-diazolidine-2,4-dione; and 1-(2-methoxy-4-fluorophenyl)-3-methyl-5-(1-2',4'-dichlorophenylamino-2,2,2-trichloroethyl)imino-1,3-diazolidine-2,4-dione;

Similarly by following the same procedure but respectively using the corresponding 3-ethyl; 3-prop-2'-enyl; 3-but-3'-ynyl-3-methoxymethylene, and 3-cyclopentyl compounds of formula A as starting materials the corresponding 3-ethyl; 3-prop-2'-enyl; 3-but-3'-ynyl; 3-methoxymethylene and 3-cyclopentyl derivatives of the above products are prepared.

Similarly the reverse 1-position-3-position isomers of each of the above prepared compounds are prepared by using the corresponding position isomers of formula A as the starting material. For example by using 1-methyl-3-(2,4-dichlorophenyl)-5-(1,2,2,2-tetrachloroethyl)imino-1,3-diazolidine-2,4-dione in place of 1-(2,4-dichlorophenyl)-5-(1,2,2,2-tetrachloroethyl)imino-1,3-diazolidine-2,4-dione the reverse 1,3 position isomer, 1-methyl-3-(2,4,dichlorophenyl)-5-(1-2',4'-dichlorophenylamino-2,2,2-trichloroethyl)imino-1,3-diazolidine-2,4-dione, is prepared.

EXAMPLE 8

This example illustrates the herbicidal properties of the compounds of Formula 1.

PRE-EMERGENT HERBICIDE TEST

Pre-emergence herbicidal activity was determined in the following manner.

An acetone solution of the imidazolidinedione test compound was prepared by mixing 750 mg of the test compound, 220 mg of a nonionic surfactant and 25 ml of acetone. This solution was added to approximately 125 ml of water containing 156 mg of surfactant.

Seeds of the test vegetation were planted in a pot of soil and the imidazolidinedione test solution was sprayed uniformly onto the soil surface at a dose of 100 mcgm/c$^2$. The pot was watered and placed in a greenhouse. The pot was watered intermittently and was observed for seedling emergence, health of the emerging seedlings, etc., for a 3-week period. At the end of this period, the herbicidal effectiveness of the imidazolidinedione test compound was rated based on the physiological observations. A 0-to-100 scale was used, 0-representing no phytotoxicity and 100 representing complete kill. The results of these tests are summarized in Table 1, hereinbelow.

POST-EMERGENT TEST

The test compound was formulated in the same manner as described above for the pre-emergent test. The concentration of the test compound in this formulation was 5000 ppm. This formulation was uniformly sprayed on 2 similar pots of 24-day-old plants (approximately 15 to 25 plants per pot) at a dose of 33 micrograms/cm$^2$. After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill. The results of these tests are summarized in Table II.

The compounds tested are identified in Table A and the results of these tests are summarized in Table 1 with respect to pre-emergent herbicidal activity and Table 2 with respect to post-emergent herbicidal activity.

TABLE A

| Compound ID No. | Compound |
|---|---|
| 1 | 1-(2-fluorophenyl)-3-methyl-5-(1-2'-fluorophenylamino-2,2,2-trichloroethyl)imino-1,3 diazolidine-2,4-dione |
| 2 | 1-phenyl-3-methyl-5-(1-phenylamino-2,2,2-trichloroethyl)imino-1,3 diazolidine-2,4-dione |
| 3 | 1-(2-fluorophenyl)-3-methyl-5-(1-dimethylamino-2,2,2-trichloroethyl)imino-1,3 diazolidine-2,4-dione |
| 4 | 1-phenyl-3-methyl-5-(1-3',4'-dichlorophenylamino-2,2,2-trichloroethyl)imino-1,3 diazolidine-2,4-dione |
| 5 | 1-(2-fluorophenyl)-3-methyl-5-(1-3',4'-dichlorophenylamino-2,2,2-trichloroethyl)imino-1,3 diazolidine-2,4-dione |
| 6 | 1-phenyl-3-methyl-5-(1-2',4'-dichlorophenylamino-2,2,2-trichloroethyl)imino-1,3 diazolidine-2,4-dione |
| 7 | 1-(2-fluorophenyl)-3-methyl-5-(1-2',4'-dichlorophenylamino-2,2,2-trichloroethyl)imino-1,3 diazolidine-2,4-dione |

TABLE 1

Pre-Emergence Herbicidal Activity - (Method 300)

| Compound ID No. | Concentration Micrograms Per cm² | Broad-Leaf Plants % kill | | | Grasses % kill | | |
|---|---|---|---|---|---|---|---|
| | | Mustard | Pigweed | Lambsquarter | W. Oats | Watergrass | Crabgrass |
| 1 | 33 | 100 | 100 | 100 | 100 | 100 | 100 |
| | 11 | 99 | 100 | 98 | 98 | 82 | 43 |
| | 3.7 | 95 | 95 | 80 | 28 | 27 | 13 |
| | 1.2 | 12 | 32 | 23 | 0 | 3 | 0 |
| 2 | 33 | 100 | 100 | 100 | 90 | 85 | 100 |
| | 11 | 92 | 98*1 | 92 | 87 | 53 | 67 |
| | 3.7 | 53 | 72 | 37 | 23 | 20 | 13 |
| | 1.2 | 0 | 27 | 0 | 0 | 17 | 0 |
| 3 | 33 | 100 | 100 | 100 | 100 | 100 | 100 |
| | 11 | 100 | 97*2 | 99 | | | |
| | 3.7 | 100 | 98*2 | 99 | | | |
| | 1.2 | 53 | 86*3 | 91 | | | |
| 4 | 33 | 100 | 100 | 100 | 60 | 50 | 95 |
| | 11 | 43 | 17 | 30 | 13 | 10 | 7 |
| | 3.7 | 3 | 0 | 7 | 0 | 3 | 0 |
| | 1.2 | 0 | 0 | 0 | 0 | 0 | 0 |
| 5 | 33 | 100 | 100 | 100 | 98 | 100 | 100 |
| | 11 | 100 | 100 | 97 | 100 | 82 | 43 |
| | 3.7 | 67 | 67 | 77 | 22 | 7 | 0 |
| | 1.2 | 17 | 0 | 23 | 0 | 0 | 0 |
| 6 | 33 | 100 | 100 | 100 | 65 | 65 | 100 |
| | | 47 | 40 | 57 | 0 | 17 | 47 |
| | | 7 | 0 | 0 | 0 | 3 | 7 |
| | | 0 | 0 | 0 | 0 | 0 | 0 |
| 7 | 33 | 100 | 100 | 100 | 100 | 100 | 100 |
| | | 100 | 97 | 94 | 98 | 83 | 53 |
| | | 53 | 50 | 37 | 23 | 13 | 0 |
| | 0 | 0 | 0 | 0 | 0 | 0 | 0 |
| Control | 0 | 0 | 0 | 0 | 0–7 | 0–7 | 0 |

*1 late germination
*2 late germination 1 replica only
*3 late germination 2 replicas only

TABLE 2

Post-Emergence Herbicidal Activity - (Method 305)

| Compound ID No. | Concentration Micrograms Per cm² | Broad-Leaf Plants % kill | | | Grasses % kill | | |
|---|---|---|---|---|---|---|---|
| | | Mustard | Pigweed | Lambsquarter | W. Oats | Watergrass | Crabgrass |
| 1 | 33 | 100 | 95 | 100 | 20 | 10 | 10 |
| | 11 | 32 | 0 | 27 | 0 | 0 | 0 |
| | 3.7 | 13*1 | 0 | 10 | 0 | 0 | 0 |
| | 1.2 | 10*1 | 0 | 0 | 0 | 0 | 0 |
| 2 | 33 | 40 | 40 | 15 | 0 | 0 | 0 |
| 3 | | 95 | 90 | 95 | 10 | 10 | 10 |
| | 11 | 67 | 27 | 83 | 10 | 20 | 0 |
| | 3.7 | 30 | 27 | 7 | 10 | 0 | 0 |
| | 1.2 | 17 | 23 | 10 | 7 | 7 | 0 |
| 4 | 33 | 55 | 40 | 10 | 10 | 10 | 10 |
| 5 | 33 | 100 | 85 | 75 | 0 | 0 | 0 |
| | 11 | 30 | 30*2 | 27 | 0 | 0 | 0 |
| | 3.7 | 10*1 | 10 | 10 | 0 | 0 | 0 |
| | 1.2 | 0 | 0 | 0 | 0 | 0 | 0 |
| 6 | 33 | 50 | 40 | 80 | 0 | 0 | 0 |
| 7 | 33 | 100 | 100 | 90 | 50 | 35 | 20 |
| | 11 | 38 | 7 | 37 | 7 | 0 | 0 |
| | 3.7 | 0 | 0 | 0 | 0 | 0 | 0 |
| | 1.2 | 0 | 0 | 0 | 0 | 0 | 0 |
| Control | 0 | 0 | 0 | 0 | 0 | 0 | 0 |

Footnotes:
*1–10% compacted
*2–20% stunted

As can be seen from the above Tables 1 and 2 the compounds of the invention generally exhibit good pre-emergence herbicidal activity against broad-leaf plants and at higher concentrations generally exhibit good pre-emergence herbicidal activity against grasses and post-emergence herbicidal activity against broad-leaf plants. However, the compounds exhibit virtually no post-emergence herbicidal activity against grasses. This lack of post-activity against grasses facilitates the use of these compounds as fungicides to treat or protect grasses infected with or subject to fungus attack.

EXAMPLE 9

In this example the fungicidal activity of the number of the compounds, of Formula A, were tested for effectiveness against spores of *Monilina fructicola* by means of a variation of "The Standard Spore Slide—Germination Method for Determining Fungicidal Activity", described in the "American Phytopathological Society Journal", Vol. 33, 627–632 (1943) unless otherwise indicated. This method measures the fungitoxic activity of fungicidal chemicals, their activity being expressed in terms of percent inhibition of germination of fungus spores. The compounds tested were dissolved in acetone to a concentration indicated in Table 3, hereinbelow. The solutions were pipetted into the wells of depression slides and allowed to dry. The wells were filled with a suspension of the fungus spores. The spores were then incubated in a moist chamber overnight. A group of 100 spores was examined and the number of spores germinated and not germinated was counted and recorded to show the biological activity in terms of the percent germination inhibition.

TOMATO EARLY BLIGHT

Activity against tomato early blight, *Alternaria solani condidia* was determined in the following manner. Tomato (v. Bonny Best) seedlings of 6 to 7 weeks old were used. The tomato plants were sprayed with a 100 ppm solution of the test compound in an acetone-and-water solution containing a small amount of a monionic emulsifier. The sprayed plants were inoculated one day later with the organism, dried and maintained at 60–80% relative humidity for about 12 days. Percent disease control was based on the percent disease development on untreated check plants.

Celery Late Blight

The celery late blight tests were conducted using celery (Utah) plants 11 weeks old. The celery late blight organism was *Septoria apii*. The celery plants were sprayed with a 150 ppm solution of the test compound mixed in an acetone-and-water solution containing a small amount of a nonionic emulsifier. The plants were then inoculated with the organism and placed in an environmental chamber and incubated at 66°–68° F. in 100% relative humidity for an extended period of time (approximately 48 hours). Following the incubation the plants were allowed to dry and then were maintained at a 60–80% relative humidity for approximately 14 days.

The percent disease control provided by a given test compound is based on the percent disease reduction relative to untreated check plants. The results are reported in Table 3.

LEAF RUST

The leaf rust test was made using pinto beans. The pathogen was *Uronyces phaseoli tipica*. The pinto bean plants were sprayed with a 250 ppm solution of the test compound in an acetone-water mixture containing a nonionic emulsifier. The treated plants were inoculated thereafter with the pathogen and then incubated in an environmental chamber of approximately 20 hours at 100% relative humidity and a temperature of 68°–70° F. The plants were then removed from the chamber, allowed to dry, and then maintained in a greenhouse at a 60–80% relative humidity. The rate of infection on the leaves was made after about 14 days. The percent disease control provided by a given test compoundf was based on the disease reduction relative to untreated check plants. The results are summarized in Table 3 hereinbelow.

(The compounds tested are identified in Table A of Example 8 hereinabove.)

TABLE B

| Fungi Identifying Code Letter | |
|---|---|
| Code Letter | Fungus |
| P | Pythium |
| H | Helminthia |
| F | Fusarium |
| R | Rhizoctonia |
| M | *Monilinia Fructicola* |
| A | Alternia |
| TLB | Tomato Leaf Blight |
| BPM | Bean Powdery Mildew |
| BR | Bean Rust |
| CLB | Celery Leaf Blight |
| SBR | Systemic Bean Rust |

TABLE 3

FUNGICIDAL ACTIVITY

| Compound ID No. | Concentration ppm | % Kill(??) - Fungus Identification Letter | | | | | | | | | | |
|---|---|---|---|---|---|---|---|---|---|---|---|---|
| | | P | H | F | R | M | A | TLB | BPM | BR | CLB | SBR |
| 1 | 250 | — | 99 | — | 100 | — | — | 44 | 4 | 64 | 50 | 69% |
| | 100 | — | 14 | — | 80 | — | — | — | — | — | — | — |
| | 40 | 0 | 2 | — | 58 | — | — | — | — | — | — | — |
| | 16 | 0 | 0 | — | 20 | — | — | — | — | — | — | — |
| | 10 | — | — | — | — | 0 | 0 | — | — | — | — | — |
| | 6.4 | 0 | — | — | — | — | — | — | — | — | — | — |
| 2 | 250 | — | 40 | 0 | 94 | | | 79 | 2 | 76 | 0 | 97% |
| | 100 | — | — | — | 4 | | | 17 | — | — | — | — |
| | 40 | — | — | — | 0 | — | — | 12 | — | — | — | — |
| | 16 | — | — | — | 0 | — | — | 5 | — | — | — | — |
| | 10 | — | — | — | — | 100 | 0 | — | — | — | — | — |
| 3 | 250 | — | 99 | 22 | 100 | | | 29 | 4 | 76 | 23 | 98% |
| | 100 | — | 14 | — | 100 | | | | | | | |
| | 40 | 0 | 2 | — | 52 | | | | | | | |
| | 16 | 0 | — | — | 20 | | | | | | | |
| | 10 | — | — | — | — | 0 | 0 | | | | | |
| | 6.4 | 0 | 0 | | | | | | | | | |
| 4 | 250 | — | 60 | 0 | 99 | — | — | 14 | 2 | 76 | 37 | 0% |
| | 10 | — | — | — | — | 0 | 0 | — | — | — | — | — |
| 5 | 250 | — | 61 | 0 | 100 | | | 44 | 2 | 47 | 11 | 0% |
| | 10 | — | | | | 0 | 0 | | | | | |
| 6 | 250 | — | 78 | 40 | 85 | | | 29 | 2 | 98 | 37 | 0% |
| | 10 | — | | | | 78 | 0 | | | | | |
| 7 | 250 | 0 | 0 | 0 | 99 | 0 | 0 | 44 | 18 | 23 | 64 | 84% |
| | 10 | — | | | | | | | | | | |

As can be seen from Table 3, although the compounds of the invention do not exhibit broad spectrum fungicidal activity, they generally exhibit good activity against Rhizoctonia. The compound also generally exhibits moderate to strong fungicidal activity against Helminthia, tomato leaf blight, bean rust, celery leaf blight and in some instances systemic bean rust.

Obviously, many modifications and variations of the invention described hereinabove and below in the claims, can be made without departing from the essence and scope thereof.

What is claimed is:

1. A compound having the formula

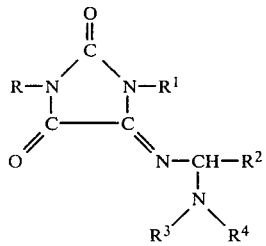

(I)

wherein one of R or $R^1$ is a lower alkyl; lower alkenyl; lower alkynyl; lower alkoxyalkylene, cyclopentyl, or cyclohexyl and the other is aryl having from 6 to 14 carbon atoms, lower aralkyl or substituted aryl having from 6 to 14 carbon ring atoms and at least one substituent independently selected from the group consisting of fluoro, chloro, bromo, nitro, $C_1$–$C_4$ alkyl, trifluoromethyl, cyano, lower alkyl amino, di(lower alkyl)amino, $C_1$–$C_4$ alkoxy, provided that said substituted aryl shall have no more than five halo, three nitro, three $C_1$–$C_4$ alkyl, two cyano, one alkylamino or di(lower alkyl)amino, or three $C_1$–$C_4$ alkoxy substituents;

$R^2$ is haloalkyl having one or two carbon atoms and from one through five substituents each independently selected from the group of chloro and bromo;

$R^3$ and $R^4$ are independently selected from the group of hydrogen and the same group of substituents as defined for R and $R^1$, provided, however, that only one of $R^3$ or $R^4$ can be hydrogen, or $R^3$ and $R^4$ together with the nitrogen atom to which they are joined form a piperidinyl or pyrrolidinyl ring.

2. The compound of claim 1, wherein R is lower alkyl.

3. The compound of claim 1 wherein R is selected from the group consisting of methyl, ethyl and allyl.

4. The compound of claim 3, wherein R is methyl.

5. The compound of claim 1 wherein $R^1$ is selected from the group consisting of phenyl; 2-fluorophenyl; 3,5-dichlorophenyl; and 3-trifluoromethylphenyl.

6. The compound of claim 5, wherein $R^1$ is 2-fluorophenyl.

7. The compound of claim 5, wherein $R^1$ is phenyl.

8. The compound of claim 1 wherein $R^1$ is lower alkyl.

9. The compound of claim 1 wherein $R^1$ is selected from the group consisting of methyl, ethyl, and allyl.

10. The compound of claim 9 wherein $R^1$ is methyl.

11. The compound of claim 1 wherein R is selected from the group consisting of phenyl; 2-fluorophenyl; 3,5-dichlorophenyl; and 3-trifluoromethylphenyl.

12. The compound of claim 1 wherein R is 2-fluorophenyl.

13. The compound of claim 1 wherein R is phenyl.

14. The compound of claim 1 wherein $R^2$ is selected from the group consisting of trichloromethyl; bromodichloromethyl; 1,1-dichloroethyl; and chloromethyl.

15. The compound of claim 14 wherein $R^2$ is trichloromethyl.

16. The compound of claim 1, wherein one of $R^3$ or $R^4$ is hydrogen and the other one is selected from the group consisting of phenyl; 2-chlorophenyl; 2-fluorophenyl; 4-fluorophenyl, 3,4-dichlorophenyl; and 2,4-dichlorophenyl.

17. The compound of claim 1, wherein $R^3$ and $R^4$ are independently selected from the group of lower alkyl.

18. The compound of claim 17, wherein each of $R^3$ and $R^4$ is methyl.

19. The compound of claim 1, wherein said aryl is phenyl and said substituted aryl is a substituted phenyl.

20. The compound of claim 1, wherein R is methyl; $R^1$ is phenyl or 2-fluorophenyl; $R^2$ is 2,2,2-trichloroethyl or 2-chloroethyl; and $R^3$ and $R^4$ are each methyl or one of $R^3$ and $R^4$ is hydrogen and the other is selected from the group consisting of phenyl; 2-chlorophenyl; 2-fluorophenyl; 4-fluorophenyl, 3,4-dichlorophenyl; and 2,4-dichlorophenyl.

21. The compound of claim 1 wherein said compound is 1-(2-fluorophenyl)-3-methyl-5-(1-2',4'-dichlorophenylamino-2,2,2-trichloroethyl)imino-1,3-diazolidine-2,4-dione.

22. The compound of claim 1 wherein said compound is 1-(2-fluorophenyl-3-methyl-5-(1-dimethylamino-2,2,2-trichloroethyl)imino-1,3-diazolidine-2,4-dione.

23. The compound of claim 1 wherein said compound is 1-(2-fluorophenyl)-3-methyl-5-(1-2'-fluorophenylamino-2,2,2-trichloroethyl)imino-1,3-diazolidine-2,4-dione.

24. The compound of claim 1 wherein said compound is 1-(2-fluorophenyl)-3-methyl-5-(1,3',4'-dichlorophenylamino-2,2,2-trichloroethyl)imino-1,3-diazolidine-2,4-dione.

25. The compound of claim 1 wherein said compound is 1-phenyl-3-methyl-5-(1-phenylamino-2,2,2-trichloroethyl)imino-1,3-diazolidine-2,4-dione.

26. The compound of claim 1 wherein said compound is 1-methyl-3-(2-fluorophenyl)-5-(1-2',4'-dichlorophenylamino-2,2,2-trichloroethyl)imino-1,3-diazolidine-2,4-dione.

27. The compound of claim 1 wherein said compound is 1-methyl-3-(2-fluorophenyl)-5-(1-dimethylamino-2,2,2-trichloroethyl)imino-1,3-diazolidine-2,4-dione.

28. The compound of claim 1 wherein said compound is 1-methyl-3-(2-fluorophenyl)-5-(1-2'-fluorophenylamino-2,2,2-trichloroethyl)imino-1,3-diazolidine-2,4-dione.

29. The compound of claim 1 wherein said compound is 1-methyl-3-(2-fluorophenyl)-5-(1-3',4'-dichlorophenylamino-2,2,2-trichloroethyl)imino-1,3-diazolidine-2,4-dione.

30. The compound of claim 1 wherein said compound is 1-methyl-3-phenyl-5-(1-phenylamino-2,2,2-trichloroethyl)imino-1,3-diazolidine-2,4-dione.

31. A method of controlling broad leaf vegetation which comprises applying an herbicidally effective amount of the compound of claim 1 to such vegetation.

32. A method of controlling the germination of vegetation which comprises applying a pre-emergence herbicidally effective amount of the compound of claim 1 to the environment to be controlled.

33. A method of controlling fungi which comprises applying thereto a fungicidally effective amount of a compound of claim 1.

34. A pre-emergence herbicidal composition comprising an herbicidally effective amount of the compound of claim 1 and a compatible inert carrier.

35. A post-emergence broad leaf herbicidal composition comprising an herbicidally effective amount of the compound of claim 1 and a compatible inert carrier.

36. A fungicidal composition comprising an fungicidally effective amount of the compound of claim 1 and a compatible inert carrier.

* * * * *

UNITED STATES PATENT AND TRADEMARK OFFICE
CERTIFICATE OF CORRECTION

PATENT NO. : 4,248,620

DATED : February 3, 1981

INVENTOR(S) : Malcolm S. Singer

It is certified that error appears in the above-identified patent and that said Letters Patent are hereby corrected as shown below:

Col. 1, lines 28-29 "methyleneaminde" should read--
methyleneamide

Col. 3, line 64 "$R^5$,RHU6,$R^7$," should read $R^5$, $R^6$, $R^7$,

Col. 9, line 50 "1-4-butylphenylamino" should read--
1-4-t-butylphenylamino==

Signed and Sealed this

Fifteenth Day of September 1981

[SEAL]

Attest:

Attesting Officer

GERALD J. MOSSINGHOFF

Commissioner of Patents and Trademarks